United States Patent
Clauson et al.

(10) Patent No.: US 9,629,747 B2
(45) Date of Patent: Apr. 25, 2017

(54) DEVICES AND METHODS FOR CUTTING LENTICULAR TISSUE

(71) Applicant: Iantech, Inc., San Mateo, CA (US)

(72) Inventors: Luke W. Clauson, Redwood City, CA (US); Maria Tsontcheva Guguchkova, Harrison, NY (US)

(73) Assignee: Iantech, Inc., Reno, NV (US)

( * ) Notice: Subject to any disclaimer, the term of this patent is extended or adjusted under 35 U.S.C. 154(b) by 0 days.

(21) Appl. No.: 15/073,177

(22) Filed: Mar. 17, 2016

(65) Prior Publication Data

US 2016/0346121 A1  Dec. 1, 2016

Related U.S. Application Data

(63) Continuation-in-part of application No. 14/857,518, filed on Sep. 17, 2015.
(Continued)

(51) Int. Cl.
| | |
|---|---|
| *A61F 9/007* | (2006.01) |
| *A61F 9/00* | (2006.01) |
| *A61B 17/3205* | (2006.01) |
| *A61B 17/32* | (2006.01) |
| *A61F 9/008* | (2006.01) |

(52) U.S. Cl.
CPC ......... *A61F 9/00736* (2013.01); *A61B 17/32* (2013.01); *A61B 17/32056* (2013.01); *A61F 9/0017* (2013.01); *A61F 9/00754* (2013.01); *A61F 9/00763* (2013.01); *A61F 9/00825* (2013.01); *A61B 2017/32006* (2013.01);
(Continued)

(58) Field of Classification Search
CPC .............. A61F 9/00736; A61F 9/00825; A61F 9/00754; A61F 9/00763; A61F 9/0017; A61F 2009/00889; A61F 2009/0087; A61F 2230/0008; A61B 17/32; A61B 17/32056; A61B 2017/32006
See application file for complete search history.

(56) References Cited

U.S. PATENT DOCUMENTS

| | | | |
|---|---|---|---|
| 4,538,611 A * | 9/1985 | Kelman | ........... A61B 17/32056 604/22 |
| 4,732,150 A | 3/1988 | Keener | |

(Continued)

FOREIGN PATENT DOCUMENTS

| | | |
|---|---|---|
| WO | 2007/011302 A1 | 1/2007 |
| WO | 2012/048348 A1 | 4/2012 |

OTHER PUBLICATIONS

International Search Report and Written Opinion received for PCT Patent Application No. PCT/US2015/050820, mailed Feb. 2, 2016, 11 pages.
(Continued)

*Primary Examiner* — Melanie Tyson
*Assistant Examiner* — Rachel S Highland
(74) *Attorney, Agent, or Firm* — Jens Hoekendijk

(57) ABSTRACT

An exemplary surgical device includes an element positionable within a shaft having a lumen defined therethrough with the element movable from a stored position to a deployed position in which a larger portion of the element extends out of the distal end of the lumen. The element forming a closed loop which is positioned around the lens while the lens is within a capsular bag. The closed loop is reduced in size to form a cut in the lens.

15 Claims, 27 Drawing Sheets

Related U.S. Application Data

(60) Provisional application No. 62/051,396, filed on Sep. 17, 2014, provisional application No. 62/099,590, filed on Jan. 5, 2015.

(52) U.S. Cl.
CPC ............... *A61F 2009/0087* (2013.01); *A61F 2009/00889* (2013.01); *A61F 2230/0008* (2013.01)

(56) References Cited

U.S. PATENT DOCUMENTS

| | | | |
|---|---|---|---|
| 4,869,716 | A | 9/1989 | Smirmaul |
| 5,222,959 | A * | 6/1993 | Anis .................. A61F 9/00763 606/107 |
| 6,551,326 | B1 | 4/2003 | Van Heugten et al. |
| 6,554,843 | B1 | 4/2003 | Ou |
| 2009/0054904 | A1 | 2/2009 | Holmen |
| 2009/0204135 | A1 | 8/2009 | Cote |
| 2010/0312252 | A1* | 12/2010 | Jia ......................... A61B 18/10 606/107 |
| 2014/0074011 | A1 | 3/2014 | Charles |
| 2015/0297407 | A1 | 10/2015 | Saimovici |
| 2016/0030241 | A1 | 2/2016 | Siepser |
| 2016/0067091 | A1 | 3/2016 | Wells et al. |

OTHER PUBLICATIONS

Invitation to Pay Additional Fees received for PCT Patent Application No. PCT/US2015/050820, mailed on Nov. 25, 2015.

* cited by examiner

DEVICES AND METHODS FOR CUTTING LENTICULAR TISSUE

CROSS-REFERENCE TO RELATED APPLICATIONS

This application is a continuation in part of U.S. application Ser. No. 14/857,518, filed Sep. 17, 2015, entitled "Devices and Methods for Removal of Lenticular Tissue," which claims priority from U.S. Provisional Application No. 62/051,396, filed Sep. 17, 2014, entitled METHOD AND DEVICE FOR LENS FRAGMENTATION USING FILAMENT CUTTING IN CATARACT SURGERY, and U.S. Provisional Application No. 62/099,590, filed Jan. 5, 2015, entitled METHOD AND DEVICE FOR AB-INTERNO INTERVENTIONAL ENDOCAPSULAR FRAGMENTATION, RETRIEVAL AND EXTRACTION IN OPHTHALMIC SURGERY, all of which are hereby incorporated by reference in their entirety for all purposes.

FIELD OF THE INVENTION

This invention relates generally to surgical devices, and more specifically to the cutting lenticular tissue for extraction of lenticular or other tissue in ophthalmic surgery.

BACKGROUND OF THE INVENTION

Certain types of conventional ophthalmic surgery require breaking up lenticular tissue and solid intraocular objects, such as the intraocular lens, into pieces so that the tissue can be extracted from the eye. Extraction of lenses for cataract surgery is one of the most common outpatient surgical fields with more than 3 million cases performed annually in the United States alone. The lens resides within an anatomical structure referred to as the capsular bag, which separates the vitreous cavity from the anterior chamber (located between the capsular bag and the cornea). It is undesirable to allow fluid communication between the vitreous cavity and the anterior chamber, so during the process of extraction of the lens, care is taken to maintain the integrity of the posterior surface of the capsular bag. However, the capsular bag is composed of thin, delicate tissue. As a result, the physician must exercise extreme care in removing lens tissue to avoid unintended damage to the capsular bag. Further complicating the procedure, the lens is typically removed from the anterior surface of the capsular bag through a generally circular incision. The procedure, and the incision resulting from the procedure, is referred to as a capsulorhexis. Typically, the capsulorhexis does not exceed 2.8-3 mm in diameter. Generally, cataract surgery and other surgical procedures that treat the lens are performed by making a small incision in the edge of the cornea, providing access to the anterior chamber and to the anterior surface of the capsular bag. Afterward, capsulorhexis is performed, and then that opening is able to be utilized for surgical access to the lens.

During cataract surgery a commonly used method for lens extraction is phacoemulsification, which uses ultrasonic energy to break up the lens, after which the lens fragments are aspirated. Other methods of lens fragmentation and extraction have include the use of mechanical instruments, such as hooks or knives, or energy-delivery instruments, such as a laser, to break up the lens into fragments and then extract through an incision in the cornea in an ab-interno approach.

However, existing tools and techniques do not ensure full-thickness fragmentation of the lens. These techniques approach the lens from the anterior surface of the eye, and therefore the dissection forces exerted by mechanical instruments are limited such that they are often insufficient to accomplish a full-thickness segmentation. Further, due to the surgical approach through the incision at the edge of the cornea, a mechanical instrument is delivered at an angle substantially parallel to the plane defined by the capsulorhexis. As a result, a conventional surgical snare, loop or wire retrieval tool is not in an orientation in which that device could be looped around the lens to provide for fragmentation or extraction. Further, even if such a conventional tool could be looped around the lens, which it cannot, the wire of the snare would run the risk of applying excessive, damaging force to the capsular bag as it would be moved into position. Energy-delivery instruments are limited in their ability to cut sections of the lens which are physically close to other delicate anatomical structures such as the capsular bag. For instance, a laser is generally not used to cut the posterior edge of the lens because it is in close proximity to the posterior edge of the capsular bag, leaving a lens that is not fully fragmented and must be fragmented carefully using secondary techniques.

For these reasons, phacoemulsification has become the most popular method of lens removal. However, phacoemulsification has its own drawbacks. As fluid and substances are aspirated from the capsular bag and the anterior chamber, other fluids such as saline are inspirated to maintain a constant volume or pressure. The flow of the fluids in the eye during inspiration and aspiration may create turbulent flow which may have a deleterious effect on the tissue within the eye, such as the corneal endothelium. The ultrasonic energy used in phacoemulsification can have its own negative consequences on ocular tissue. Further, phacoemulsification requires expensive and bulky capital equipment, limiting the locations in which phacoemulsification can be performed.

BRIEF SUMMARY OF THE INVENTION

The present disclosure recognizes that existing techniques for removing lenticular tissue are generally cumbersome and inefficient. Further, in order to overcome the risks of damaging the capsular bag with existing techniques, the lens is not completely broken up or dissolved, leaving one or more fragments sized larger than clinically desirable.

Therefore, the present disclosure provides for devices and methods that effectively break up the lens into small fragments and capture those fragments. Such devices and methods optionally complement or replace other devices or methods for eye surgery. Such methods and interfaces reduce the risk of damage to ocular tissue, such as the capsular bag, and produce a more efficient surgical experience.

In some embodiments, a surgical device includes a shaft with a lumen defined therethrough; and an element movable from a stored position to a deployed position in which a larger portion of the element extends out of an outlet at the distal end of the lumen; wherein motion from the stored position to the deployed position causes a first leg of the element to advance distally relative to the distal end of the shaft, and causes a second leg of the element to move proximally relative to the distal end of the shaft.

In some embodiments, a device for surgery on a human eye (which includes a capsular bag, a lens inside the capsular bag, and a cornea) includes a tube with a lumen defined therethrough; and a sectioning element configured to change between at least a first shape and a second shape, the second shape having a perimeter, and the sectioning element extending from the distal end of the lumen; wherein the first shape is sized to insert through a capsulorhexis on the anterior surface of the capsular bag, the diameter of is the capsulorhexis less than the diameter of the lens; wherein the sectioning element is movable from the first shape to the second shape to move between the lens and the capsular bag, such that when the sectioning element has the second shape, the sectioning element includes at least a portion of the lens within its perimeter; and wherein the sectioning element is movable to a third shape from the second shape to apply cutting force to the lens.

In some embodiments, a device for eye surgery includes a shaft with a lumen defined therethrough; an inner rotating element positioned at least partially in the lumen; an outer rotating element positioned at least partially in the lumen, and positioned radially between the inner rotating element and the shaft a first plurality of straps extending distally from the distal end of the outer rotating element, each of the first plurality of straps circumferentially spaced from one another; a second plurality of straps extending distally from the distal end of the inner rotating element, each of the second plurality of straps circumferentially spaced from one another; and a tip connected to the distal end of each of the straps; wherein the first plurality of straps and second plurality of straps are movable from a closed position to an open position; and wherein at least one of the first plurality of straps and second plurality of straps is rotatable relative to the other in the op en position.

DETAILED DESCRIPTION OF THE INVENTION

Figure 1:
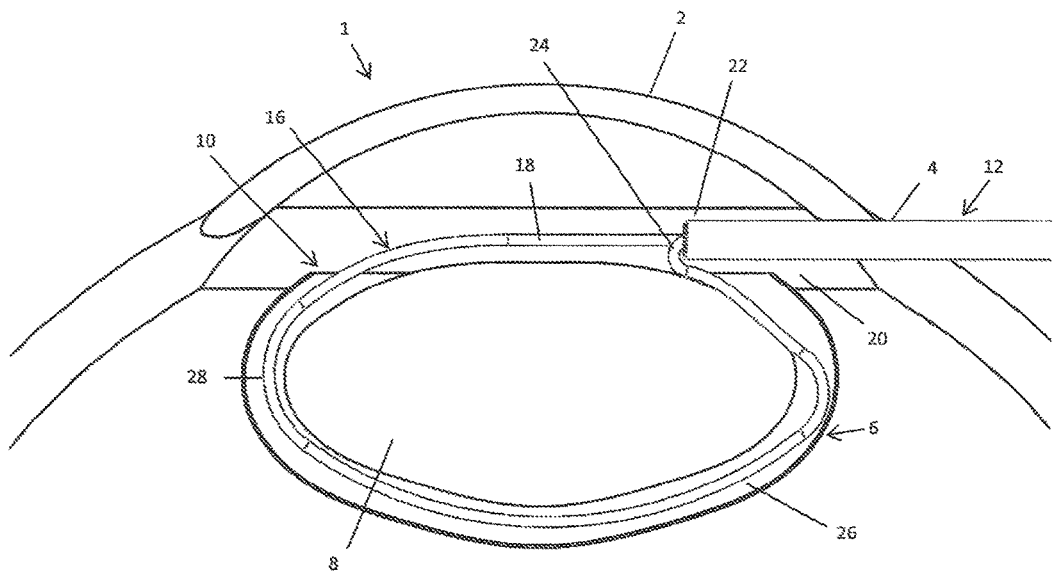
FIG. 1 is a side schematic view of the ocular anatomy, showing the insertion of a shaft and sectioning element through an incision in the side of the cornea.
Figure 3:
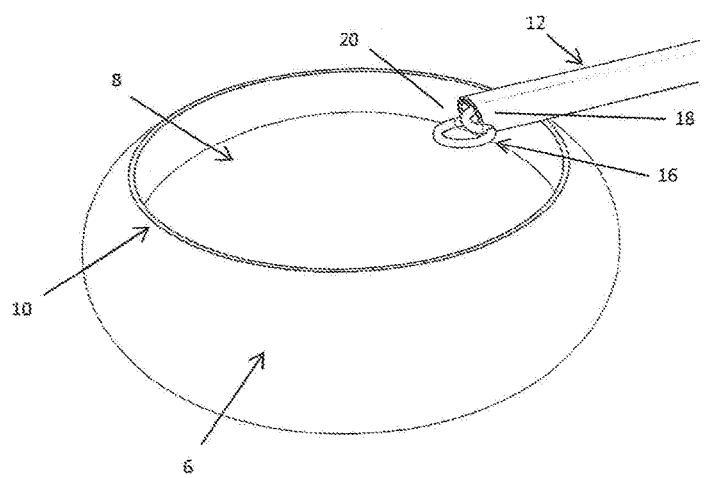
FIG. 3 is a perspective view of the capsular bag, with a completed capsulorhexis, with a sectioning element in a first, insertion configuration.

Referring to FIG. 1, the normal anatomy of the eye 1 includes a cornea 2, capsular bag 6, and a lens 8 within the capsular bag 6. An incision 4 is made in the edge of the cornea 2, and the surgeon performs a capsulorhexis procedure on the capsular bag 6, resulting in a capsulorhexis 10 in the anterior surface of the capsular bag 6. The capsulorhexis 10 may be performed in any suitable manner, such as incising with a scalpel, applying energy with a femtosecond laser or other energy-based cutter, incising under robotic or automated control, or in any other suitable manner. The capsulorhexis 10 can be torn or cut in a diameter of approximately 2.0 mm to 8.0 mm. According to other embodiments, the capsulorhexis 10 may be made smaller in diameter than 2.0 mm, particularly where fragments of the lens 8 (as described in greater detail below) are small enough in size to be extracted through a smaller-diameter capsulorhexis 10. The capsulorhexis 10 can be made with a separate set of instruments such as micro-forceps, as is commonly done. Alternatively, features and tools can be incorporated into the surgical device 40 described herein to facilitate or completely perform the capsulorhexis. For example, micro-forceps could be added to the distal end of the shaft 12 such that the tool 40 can perform the capsulorhexis. As other examples, one or more of a blade, keratome, hook, laser, ablative energy applicator, or the like can be incorporated into or associated with the distal end of the shaft 12 for use during surgery. For example, an extending tip may be attached to the shaft 12, and used to rotate the lens 8 between fragmentation steps as described herein. The extending tip may be a sharp tip which can be pierced into the lens 8 such that the user can rotate the lens 8 to a new orientation and section the lens 8 from a different angle. According to some embodiments, any separate tools used by the surgeon to perform the capsulorhexis are removed out of the incision 4 in the cornea 2. Referring also to FIG. 3, a shaft 12 is then inserted through the incision 3 in the cornea 2. As seen in FIG. 3, the distal end of the shaft 12 is positioned above (i.e., anterior to) the capsulorhexis 10, spaced apart from the capsulorhexis 10 but positioned within the circumference of the capsulorhexis 10 as viewed from outside the eye 1. As seen in FIG. 1, the shaft 12 is generally parallel to the plane defined by the edges of the capsulorhexis 10 upon its insertion through the incision 3 in the cornea 2. In some embodiments, the distal end of a sectioning element 16 extends out of an outlet 5 in a lumen 14 at the distal end of the shaft 12 in a first, insertion configuration. In such embodiments, the tight radius bend 24 may be positioned outside the shaft 12, already bent at least partially toward the proximal direction. In this way, even in embodiments where the sectioning element 16 is fabricated from superelastic material, the angle through which the second leg 20 of the sectioning element 16 is bent during transition from the first, insertion configuration to the second, capture configuration is reduced. Further, less space is required within the lumen 14 of the shaft 12 to hold part of the sectioning element 16 than to hold all of it, allowing the shaft 12 to be made smaller in diameter. According to some embodiments, the shaft 12 is an ovular cross-section tube with a rounded tip. The ovular cross-section enhances the ability of the shaft 12 to be inserted into the eye 1 through the corneal incision 4. Additionally, in the event that there are multiple sectioning elements, they may be arranged side-by-side more easily in the lumen 14 of an ovular cross-section shaft 12. Alternately, the shaft 12 may have a circular cross-section or a cross-section of any other suitable shape. The proximal end of the sectioning element 16 extends through the lumen 14 of the shaft 12. Alternately, the entirety of the sectioning element 16 is positioned within the lumen 14 of the shaft 12 in the first, insertion configuration. Alternately, more than one sectioning element 16 is utilized, where each sectioning element 16 is initially in the first, insertion configuration. While a single sectioning element 16 is described with regard to this particular embodiment for clarity, it will be apparent in light of the further disclosure below that any suitable number of sectioning elements 16 may be provided and used in a single lens removal procedure, and that the devices and methods herein are not limited to the use of any particular number of sectioning elements 16.

According to some embodiments, the sectioning element 16 includes a first end 18 and second end 20. As described in greater detail below with regard to FIGS. 16-22, one of the ends 18, 20 of the sectioning element 16 may be movable relative to the shaft 12, while the other of the ends 18, 20 of the sectioning element 16 may be fixed relative to the shaft 12. For example, the second end 20 of the sectioning element 16 may be fixed relative to the shaft 12 and the first end 18 of the sectioning element 16 may be slidable relative to the shaft 12. The second end 20 may be connected to the shaft 12 or to other structure by crimping, welding, adhesives, mechanical interlocks, or any other suitable structure or method. In some embodiments, the sectioning element 16 is a wire with a circular, oval or other atraumatic cross-section. In other embodiments, the sectioning element 16 is a strap. As used in this document, a strap is a structure that is wider than it is thick, as viewed longitudinally.

In the first, insertion configuration, where the distal end of the sectioning element 16 extends distally out of the shaft 12, the sectioning element 16 is sized and shaped to pass through a standard corneal incision 4 without damaging the eye 1. The corneal incision 4 is generally 3.5 mm or less in width and made with a small knife. Thus, the outer diameter of the shaft 12 advantageously is 3.5 mm or less. Where a differently-sized incision 4 is used, a different outer diameter of shaft 12 may be used, keeping in mind that it is most desirable to form the incision 4 as a line 5 mm or less in length. In other embodiments, the sectioning element 16 is positioned completely within the lumen 14 of the shaft 12 such that it is within the inner diameter of the shaft 12 as the shaft 12 is inserted through the incision 4, and is then extended out of the shaft 12 once in the eye. Alternatively, additional components may be used to sheath the sectioning element 16 during insertion through the corneal incision. 4.

For example, a tapered piece may be positioned on the distal end of the shaft 12 which gradually tapers from the end of the shaft 12 down to a smaller cross section such that it can aid insertion through the corneal incision 4. The tapered piece can also cover the sectioning element 16 to constrain it during insertion. The tapered piece can further have a slit in the front which the sectioning element 16 can extend through or tear open once it has passed through the incision 4.

According to some embodiments, the sectioning element 16 is fabricated from of a flexible or superelastic material, such as nickel-titanium alloy, which allows the sectioning element 16 to bend and flex as it is inserted into the eye 1 through the corneal incision 4. In these embodiments, the constricted shape of the sectioning element 16 may be larger in one or more dimensions than the corneal incision 4, and flexes to pass through the incision 4 as the shaft 12 moves toward the capsulorhexis 10. Alternatively, the sectioning element 16 may not have a first, insertion configuration, and may be inserted through the incision 4 in the same configuration that is later utilized to engage the lens 8. In such embodiments, the sectioning element 16 compresses as it passes through the corneal incision 4 and then re-expands once it enters the eye 1. In still other embodiments, the sectioning element 16 may not have a first, insertion configuration, and may be inserted through the incision 4 in a larger configuration than is later utilized to engage the lens 8. In still other embodiments, the sectioning element 16 may be hooked, rotated, or otherwise inserted through the corneal incision 4 in any number of methods.

Figure 4:
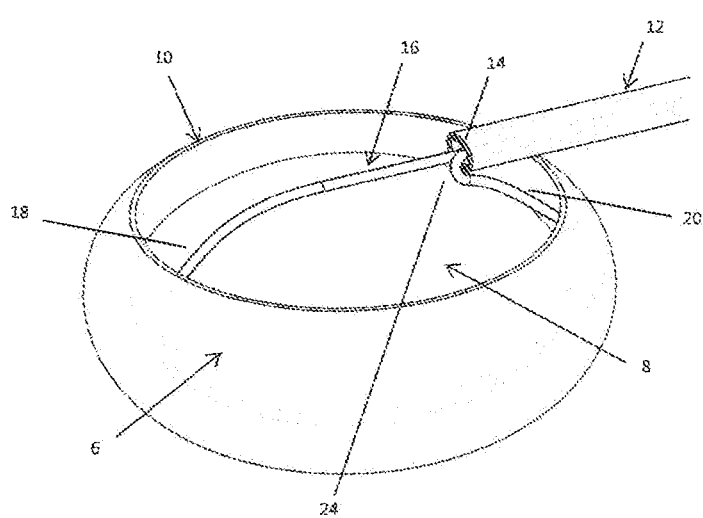
FIG. 4 is a perspective view of the capsular bag, with a completed capsulorhexis, with a sectioning element in a second, capture configuration.

Referring to FIG. 4, the sectioning element 16 or elements are pushed distally relative to the lumen 14 of the shaft 12. As set forth above, one leg 20 of the sectioning element 16 may be fixed, such that the other leg 18 of the section element 16 is pushed distally relative to the lumen 14 of the shaft 12. As a result, the sectioning element 16 moves from a first, insertion configuration to a second, capture configuration.

The sectioning element 16 may be fabricated from any suitable material. For example, as discussed above, shape memory materials such as nickel-titanium alloy may be used to allow the sectioning element 16 to move to its predefined shape in the second, capture configuration, with a high amount of elasticity. In one embodiment, the nickel-titanium alloy may be used in its superelastic condition, where the nickel-titanium alloy transforms its crystal structure to move from the first, insertion configuration to the second, capture configuration. In other embodiments, the sectioning element 16 is fabricated from nickel-titanium alloy that is shape set to move from the first, insertion configuration to the second, capture configuration upon reaching a transition temperature that is above room temperature but below body temperature. The sectioning element 16 fabricated from nickel-titanium alloy thus may enter the eye at room temperature below its transition temperature such that it will hold a constricted shape. As the sectioning element 16 is placed into the eye 1 and allowed to warm to body temperature, the nickel-titanium alloy may become warmer than its transition temperature and begin to return to its predefined second, capture configuration. This shape change may happen over a period of time that allows the surgeon to place the sectioning element into the capsular bag 6 and orient it while the shape changes such that the loop can define a sectioning plane through the lens. Alternatively, any other number of biocompatible materials may be considered such as stainless steel. In some embodiments, the nickel-titanium alloy may be warmed actively by the surgical device 40, in which case the transition temperature of the sectioning element 16 may be selected to be greater than room temperature but less than a temperature that would damage the tissue of the capsular bag 6 or other tissue of the eye 1. Other shape memory materials such as shape memory plastics may be utilized instead of nickel-titanium alloy. Alternatively, any other number of biocompatible materials may be considered such as stainless steel, titanium, silicone, polyimide, PEBAX® poly ether block amide, nylon, polycarbonate, or any other suitable material. Furthermore, multiple materials joined end to end or in laminated layers or concentric tubes of material may be used.

Referring also to FIGS. 1 and 4, in the second, capture configuration, the sectioning element 16 is specifically shaped for lens capture. According to some embodiments, the second, capture configuration is a preset shape of the sectioning element 16, such as through the use of elastic or superelastic materials to fabricate the sectioning element.

As seen most clearly in FIG. 4, in the second, capture configuration, the sectioning element 16 approximates an irregular loop that is generally shaped like the cross-section of a lens 8, and that is shaped and sized to surround the lens 8 within the capsular bag 6. As set forth above, in some embodiments, the sectioning element 16 is fabricated from a length of round wire. The second, capture configuration of the sectioning element 16 has a merging point 22 where the first leg 18 and second leg 20 of the sectioning element 16 merge back together, forming a shape with a perimeter so that the device 40 approximates a closed loop 21. The "merging" refers to placing the first leg 18 and second leg 20 of the sectioning element 16 into proximity with one another. The merging point 22 may be located at or in proximity to the distal end of the shaft 12. In the second, capture configuration, the sectioning element includes a distal portion 28 that extends distal to the merging point 22 and a proximal portion 26 that extends proximally to the merging point 22. The merging point 22 in this exemplary embodiment is at a point above the surface of the lens and within the circle defined by the capsulorhexis 10 at the top of the capsular bag 6. In some embodiments, the proximal portion 26 of the sectioning element 16 may include a tight radius bend 24 as shown in FIG. 1. The tight radius bend 24 bends the second leg 20 of the sectioning element 16 proximally such that the second leg 20 extends proximally from the merging point 22. Alternatively, the sectioning element 16 may take a different path to achieve this path transition without such a sharp radius bend. For example, paths which are outside of the normal plane of FIG. 1 such as curves or oscillations may be incorporated to reduce the overall bend radius of the proximal portion 26 of the sectioning element 16. This may improve the ability of the sectioning element 16 to change shape into other smaller constricted configurations as will be discussed below.

The first leg 18 and/or second leg 20 is pushed out of the lumen 14 of the shaft 12, while the other leg is fixed relative to the shaft, as described above. Alternatively, both legs 18, 20 of the sectioning element 16 are movable relative to the shaft 12 and configured to slide relative to the lumen 14 of the shaft 12. Alternatively, the shaft 12 may be the sliding component while the sectioning element 16 remains stationary. As the leg or legs 18, 20 are pushed outward from the lumen 14, the sectioning element 16 transitions to the second, capture configuration. As the sectioning element 16 transitions, the tight radius bend 24 allows the proximal section of the sectioning element to extend proximally from the distal end of the shaft 12, at a location spaced from and to one side of the longitudinal centerline of the lumen 12 in the direction toward the capsular bag 6. In this way, the sectioning element 16 is able to extend downward through the capsulorhexis 10 and expand to a length within the capsular bag 6 that is greater than the diameter of the capsulorhexis 10, as seen in FIG. 1. According to some embodiments, the tight radius bend 24 results in the second leg 20 having an angle of at least 120 degrees relative to the longitudinal centerline of the shaft 12, and relative to the distal direction, as seen in FIG. 1. Both the distal portion 28 and the proximal portion of the sectioning element 16 in the second, capture configuration are gently curved and generally approximate the size and shape of the lateral sides of the capsular bag 6, in order to enter the capsular bag 6 without causing damage (e.g., such as a capsular tear or hole, over-stretching the capsular bag, or damaging the inner surface of the capsular bag tissue).

Figure 2:
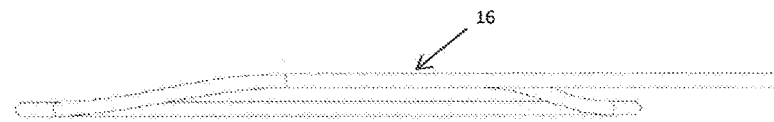
FIG. 2 is a top view of the sectioning element in a deployed position.

Referring also to FIG. 2, the shape of the sectioning element 16 in the second, capture configuration forms a plane that is generally flat or horizontal with respect to the top lens surface, according to some embodiments. Referring back to FIGS. 1 and 3, with the correct orientation, the sectioning element 16 is held such that it opens through the capsulorhexis 10 into the capsular bag 6. As the sectioning element 16 continues to expand, the plane formed by the sectioning element 16 can be rotated so that the sectioning element traverses a space between the capsular bag and the lens. The plane includes the longitudinal axis of the lumen 14 of the shaft 12. Alternately, the shape of the sectioning element 16 in the second, capture configuration is a more three-dimensional shape that does not lie in a single plane. For example, the sectioning element 16 may oscillate in and out of a flat plane, or may be substantially curved out of a flat plane in one direction or another. The rotation may be accomplished by manual rotation of the shaft 12 or surgical device 40 by the user, or may be accomplished by integrated mechanisms within the surgical device 40, as described in greater detail below. Referring also to FIG. 4, the sectioning element 16 has proceeded most of the way from the first, insertion configuration to the second, capture configuration, and has been rotated partially relative to the lens 8. The sectioning element 16 may be rotated such that the shape plane is primarily vertical or to any number of other angles. Mechanisms and methods for producing such rotation are described in greater detail below. Additionally, multiple sectioning elements 16 may be used that rotate to a variety of angles. In other embodiments, the rotation does not occur until the sectioning element 16 transitions to the second, capture configuration. According to some embodiments, rotation begins while the sectioning element 16 transitions to the second, capture configuration. For example, rotation may begin once an open area 46 of the loop and within the sectioning element 16 expands to a size in which a 5-6 mm chord extends across the open area 46 between two points on the proximal section 26 and the distal section 28. As another example, rotation may begin when the chord is longer than, or shorter than 5-6 mm.

The second, capture configuration of the sectioning element 16 may be generally ovular in shape, referring to FIG. 1, with a width 7.0-15.0 mm and a height of 3.0-10.0 mm, according to some embodiments. According to other embodiments, the width of the sectioning element 16 may be 4.0-20.0 mm with a height of 1.0-15.0 mm. In some embodiments the size of the second, capture configuration of the sectioning element 16 may be intentionally smaller than the size of the lens at certain areas or along the entire profile. This may improve the ability of the sectioning element 16 to remain close to the lens 8 and reduce interaction with the capsular bag 6. For example, the second, capture configuration of the sectioning element 16 may be 12.0 mm wide and 4.0 mm high. This may allow clearance between the sectioning element 16 and the lens 8 at the width of the oval while maintaining interference along the height of the oval which may reduce the likelihood of damaging the posterior surface of the capsular bag 6. That is, by configuring the second, capture configuration of the sectioning element 16 to engage a portion of lens 8, rather than move to a position in which it encircles the thickest part of the lens 8, the sectioning element 16 is sized smaller, and engages less of the capsular bag 6, than a configuration in which the second, capture configuration of the sectioning element 16 is able to encircle the thickest part of the lens 8. In other embodiments, the second, capture configuration of the sectioning element 16 is predefined to have a generally specific clearance around the lens 8. According to some embodiments, the second, capture configuration of the sectioning element 16 has a different shape than generally oval.

The sectioning element 16 may have features or geometry which further prevents the element from damaging the capsular bag. For example, the sectioning element 16 is a round wire of sufficient diameter to reduce the likelihood of tearing or damaging the capsular bag 6, according to some embodiments. The diameter of that round wire may be 0.004"-0.012," but may also be any size that prevents excessive stress from being placed on the capsular bag 6, such as 0.001"-0.030" diameter. Alternatively, the profile of the sectioning element 16 may be ovular with a larger width or height, or may be a strap, to further distribute the force of the sectioning element 16 on the capsular bag 6 over a larger surface area, thereby reducing or eliminating areas of high pressure exerted on the capsular bag 6 by the sectioning element.

In some embodiments, portions of the outer surface of the sectioning element 16 may be coated to improve certain aspects of the device. For example, as discussed in greater detail below, the sectioning element 16 traverses a space between the capsular bag 6 and the lens 8. As the sectioning element 16 moves between these anatomical structures it may be advantageous to have a more hydrophilic or hydrophobic surface so the sectioning element 16 rotates and moves more freely. In one embodiment, the sectioning element 16 may be coated with a hydrophobic material such as a fluoropolymer; for example, PTFE. A coating can be added through dip coating, plasma vapor deposition process, heat shrink sleeves, or any other suitable method. The coating can reduce the friction between the sectioning element 16, and the lens 8 and/or capsular bag 6, to allow the sectioning element 16 to move more freely. Other methods of reducing the friction may include using mechanical abrasion, plasma treatments, or any other suitable method. Alternatively, the sectioning element 16 may be coated with other materials such as active pharmaceutical agents which are configured to release into they during the procedure. For example, a steroid like triamcinolone may be added to the surface of the sectioning element 16 such that during the procedure it releases into the eye. Any other number of coatings and drugs may be contemplated.

The sectioning element 16 may be constructed with any other suitable geometries or materials. In an exemplary embodiment, the sectioning element 16 is a round wire. The wire is configured to bluntly traverse a sp ace between the lens 8 and the capsular bag 6. The wire can have various sizes or diameters along the length of the sectioning element 16. Alternatively, the sectioning element 16 may be any number of other profiles. For example, the sectioning element 16 could be a tube, a ribbon, a strap, a wire with a hexagonal profile, or any other number of suitable shapes. In addition, the profile of the sectioning element 16 could change along its length. For example, the sectioning element 16 may include one or more padded areas along its profile where damage to the capsular bag 4 is of particular concern. The padded areas may include different materials, such as but not limited to soft elastomeric materials like silicone that are bonded or coated onto appropriate areas of the sectioning element 16. The padded areas may distribute the force over a larger area, and provide a softer and more atraumatic interface against the capsular bag 6. In other embodiments, the padded areas are geometry profile changes of the sectioning element in certain areas. For example, areas which are flared out or broadened, even if comprised of the same material, distribute the force over a larger area. Additionally, the stiffness or flexibility of the sectioning element may vary over the sectioning element 16 by changing the material thickness or wire diameter in certain areas. Alternatively, sleeves or other materials may be added to the sectioning element 16 to increase stiffness locally in certain areas. In still other embodiments, the sectioning element 16 may have cuts or ribs along its length which change its flexibility or stiffness in certain areas.

In other embodiments, the shape of the sectioning element 16 in the second, capture configuration is not predetermined. Instead shape of the sectioning element 16 in the second, capture configuration is defined by the material or geometric properties of the sectioning element 16, engaged with the lens 8. The sectioning element 16 may be sufficiently flexible, elastic, soft, or blunt along its length, while maintaining sufficient stiffness to allow for rotation to engage the lens 8, such that minimal force is applied to the capsular bag 6 even when the sectioning element 16 is within the capsular bag 4 and fully opened. In other embodiments, the sectioning element 16 may be a soft elastomer such as silicone which may be sufficiently soft and large enough in diameter so that the sectioning element 16 does not place excessive force onto the capsular bag 6. In still other embodiments, the sectioning element 16 may be sufficiently blunt along certain portions and edges such that the force applied to the capsular bag 6 is distributed over a larger area and therefore the tearing pressure may be reduced. In still other embodiments, the sectioning element 16 may be comprised of a linkage of multiple elements, for example a chain-like structure, allowing for flexible movement between the multiple elements. In still other embodiments, the sectioning element 16 may have slits along portions of its length which locally may increase its flexibility. For example, the sectioning element 16 may include a tube with cutouts along its length at areas where the capsular bag 6 may come in contact with the sectioning element 16 such that these areas are more flexible and therefore are less prone to putting excessive force onto the capsular bag 6. In still other embodiments, portions of the sectioning element 16 in the second, capture configuration are not predetermined in shape, while other portions of the sectioning element 16 are predetermined in shape. For instance, a portion of the sectioning element 16 anterior to the lens may be fabricated from a shape memory round wire which is shape set to a predefined shape which aids in guiding the sectioning element 16 into the eye. For example, such a portion can include the tight radius bend 24 of the proximal portion 26. A portion of the sectioning element 16 posterior to the lens 8 may be fabricated from a different, more-flexible material that more easily conforms to the shape of the eye. In this way, the portion of the sectioning element 16 in the second, capture configuration that allows for insertion of the sectioning element through the capsulorhexis, including the tight radius bend, are anterior to the lens 8, and the portion of the sectioning element 16 in the second, capture configuration that contacts the capsular bag 6 is composed of more-flexible material even less likely to damage the capsular bag 6.

According to some embodiments, additional guide tubes or components may align or direct the path of the sectioning element 16 through the capsulorhexis 10 and/or around the lens 8. For example, in embodiments where the sectioning element 16 in the second, capture configuration does not have a predefined shape, a guiding element may exist along areas of the distal portion 28 or proximal portion 26 of the sectioning element 16 to constrain it into a particular shape. A tube may extend from the merging point 22 in the direction of the distal portion 28, and the tube may concentrically constrain the flexible sectioning element 16 such that it more or less follows a desired path during insertion into the capsular bag 6 and placement around the lens 4. The guiding tube may then be retracted, leaving the flexible sectioning element 16 in place around the lens 4.

In still other embodiments, the predefined shape of the sectioning element 16 in the second, capture configuration may be created during any part of the surgical procedure. For example, the surgeon may use imaging techniques to measure anatomical features of the eye such as the lens 8 or capsular bag 4. The surgeon may then use this information to or change a shape of the sectioning element. Alternatively, a piece of equipment such as a forming die or an automated wire forming machined may be used in conjunction with the measured data to change the shape of the sectioning element 16 in the second, capture configuration. In one embodiment, the surgeon uses an imaging modality such as OCT to perform a measurement of the lens 8, and then this information is provided to an automated wire forming station which creates a custom sectioning element 16 for the patient. In still other embodiments, the surgeon may add or change a shape of the sectioning element 16 while at least a portion of the sectioning element 16 is within the eye. For example, the surgeon may begin to place the sectioning element 16 into the capsular bag 6 and determine that its shape may be improved. The surgeon may then insert a separate tool such as forceps into the eye or use an integrated tool associated with the shaft 12 to add or change a shape of the sectioning element 16.

According to some embodiments, a fluid is introduced between the capsular bag 6 after the capsulorhexis 10 is made, such that a space is created between the lens 8 and capsular bag 6 in at least some areas. This may be referred to as fluid dissection, hydro dissection or space creation. According to some embodiments, the fluid creates a space for the sectioning element 16 in the second, capture configuration to be rotated within the capsular bag 6 and surround the lens 8. In an exemplary embodiment, fluids such as viscoelastic hyalarunic acid or saline may be injected since these materials are commonly used during ocular surgery, well-tolerated within the eye, and readily available. One or more other or additional fluids may be introduced, such as dyed fluids, pharmaceutical liquids like steroids, drug loaded fluids, bioabsorbable fluids, lubricants, hydro gels, microspheres, powdered substances, fluorescent contrast, liquid foams, or any other suitable fluid. Additionally, one or more gases additionally or instead may be introduced, such as air, oxygen, argon, nitrogen, or the like. Alternatively, in other embodiments a fluid space may not be required between the lens 8 and the capsular bag 6, and the sectioning element 16 may perform a mechanical dissection or blunt dissection of the lens 8 and capsular bag 4. as it is rotated about the lens 8. Fluid dissection and blunt dissection may be done in combination with one another or separately. The fluid may be injected through a cannula or a needle into the capsular bag 6 using a separate instrument. According to other embodiments, provisions for fluid dissection may be incorporated into elements of the surgical device 40, such as the sectioning element 16. For example, the sectioning element 16 may be fabricated as a flexible tube with a plurality of holes along its length that allow for the passage of fluid therethrough. In such an embodiment, fluid may be introduced into the lumen of the sectioning element 16 and then flow out of the plurality of holes. This may improve the ability of the sectioning element 16 to pass between the capsular bag 6 and the lens 8 because the fluid may be introduced through the sectioning element 16 continuously or at discrete points in time when dissection is needed. In still other embodiments, the fluid injection may be incorporated in other aspects of the surgical device 40. For example, fluid may be delivered via the lumen 14 of the shaft 12. Alternatively, a component separate from the shaft 12, such as a telescoping tube or other tube, may be connected to the shaft 12 to provide for fluid introduction. In some embodiments, the fluid which is infused through a component of the device, such as the shaft 12 or the element 16, may be used for other surgical purposes. For example, fluid may be infused through the shaft 12 to maintain the chamber of the eye 1 without the need for a separate cannula or without the need for a viscoelastic substance. Irrigation and aspiration may be accomplished through a single component or through multiple separate components. For example, fluids such as saline may be irrigated into the eye through a lumen of an embodiment of the sectioning element 16, as described above, and aspirated through the lumen of the shaft 12. Other irrigation or aspiration techniques may be performed, according to some embodiments.

Figure 5:
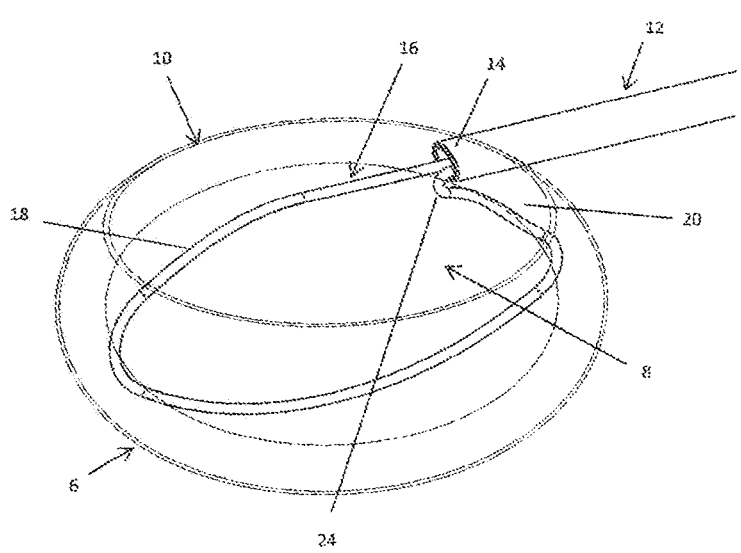
FIG. 5 is a perspective view of the capsular bag, with a completed capsulorhexis, with a sectioning element in a third, fragmentation position.
Figure 6:
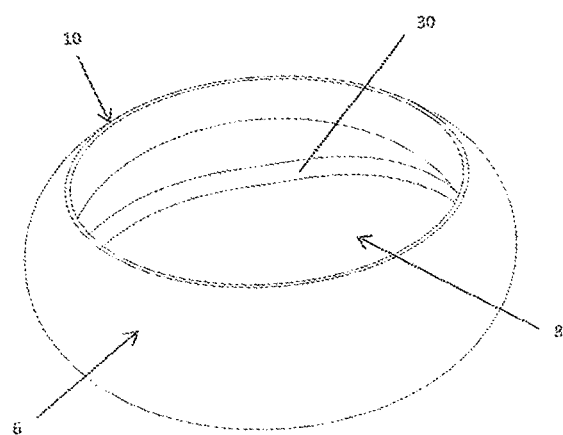
FIG. 6 is a perspective view of the lens of FIG. 5, with the sectioning element not shown for clarity.
Figure 7:
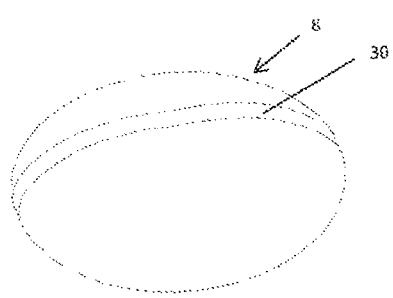
FIG. 7 is a perspective view of the lens of FIG. 5, with the sectioning element and capsular bag not shown for clarity.

Referring to FIG. 5, the sectioning element 16 has been fully extended to the second, capture configuration, and has been rotated about the longitudinal axis of the shaft 12 and/or otherwise rotated or moved to an orientation within the capsular bag 6 in which the sectioning element 16 surrounds the lens 8 without exerting excessive force onto the capsular bag 6. The sectioning element 16 is then used to cut the lens 8 by tensioning one or both legs 18, 20 of the sectioning element 16, such as by retracting one or both legs 18, 20 through the lumen 14 of the shaft 12. The sectioning element 16 may be moved in the opposite manner as set forth above for expanding the sectioning element 16 from the first to the second configuration, in order to compress and cut the lens 8. As the sectioning element 16 is tensioned, it exerts an inward force on the lens 8 and begins cutting and/or fragmenting it. due to the force applied to the lens 8 across the small surface area of the thin diameter sectioning element 16. The sectioning element 16 continues to be tensioned until the lens 8 is partially or fully sectioned. In some embodiments the sectioning element 16 is tensioned until the lens 8 is fully sectioned. In other embodiments, tensioning of the sectioning element 16 only partially fragments the lens 8, and the remainder of the lens 8 can be fragmented by repeating the use of the sectioning element, or with additional tools. Referring to FIG. 6, the fragmented lens 8 is shown within the capsular bag 6. The section plane is primarily vertical, but it should be appreciated that any number of angles and orientations may exist for the cutting path of the sectioning element 16. Referring to FIG. 7, the lens is shown with the capsular bag removed.

In some embodiments, the surgical device 40 may incorporate multiple sectioning elements 16, as described below, to create multiple lens fragments at one time. For example, the multiple sectioning elements 16 may form a mesh which is capable of cutting the lens 8 into a multitude of fragments; the sectioning elements 16 may be at oblique or acute angles relative to one another such that they form a criss-cross pattern. In other embodiments, the surgical device 40 may be used successively on the lens 8. For example, after a single section is created the lens 8 (or the sectioning element 16) can be rotated 90 degrees such that the first section plane is now perpendicular to the delivery device plane. The sectioning element 16 can then be reinserted into the capsular bag 6 as described above, and used to create a new section across the two lens fragments which creates four fragments in total. The process may be repeated for as many times as necessary to create any number of lens fragments of any desired size. The final desired size of the lens fragments may depend on method of extraction from the eye 1. In some embodiments, phacoemulsification additionally may be used in the capsular bag 6 to remove the lens fragments. This may be particularly useful in difficult or hard cataracts, where full lens fragmentation increases the surface area and decreases the size of fragments that are to be emulsified by phacoemulsification. In other embodiments, the lens fragments may be extracted as described below.

In some embodiments, the lens fragments may be pushed out of the capsular bag 6 by introducing fluid into the capsular bag 6 under slight pressure. The fluid flow and/or pressure may move the lens fragments into the anterior chamber of the eye 1, such that other tools and methods for extracting the lens may be utilized. For example, forceps or grasping tools may be used to grab the lens fragments and pull them out of the eye 1 through the corneal incision 4. In some embodiments, the sectioning element 16 may be used to snare the lens fragments and pull them out of the eye 1. The sectioning element 16 may be returned to the second, capture configuration and placed around a lens fragment. The sectioning element 16 may then be tensioned or otherwise closed until the lens 8 is held within of the sectioning element but the lens fragment is not cut. The lens fragment can then be pulled out of the eye 1 with the sectioning element 16. To ensure that the lens 8 is not cut by the sectioning element 16, additional components may be used such as pads, straps, or strips with a larger surface area that grip the lens fragment rather than cutting it. These components can be extended from the shaft 12, or may be separate components that are inserted into the eye 1 through the incision 4 and attached to the sectioning element 16.

Figure 8:
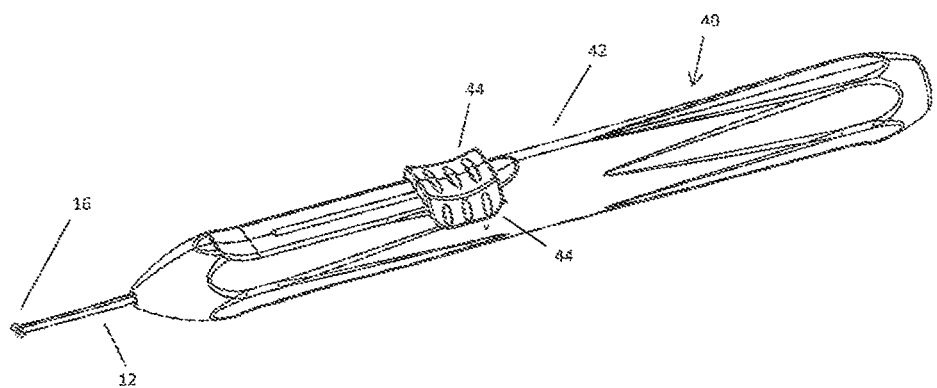
FIG. 8 is perspective view of a surgical device including a handle, shaft and multiple sectioning elements.
Figure 9:
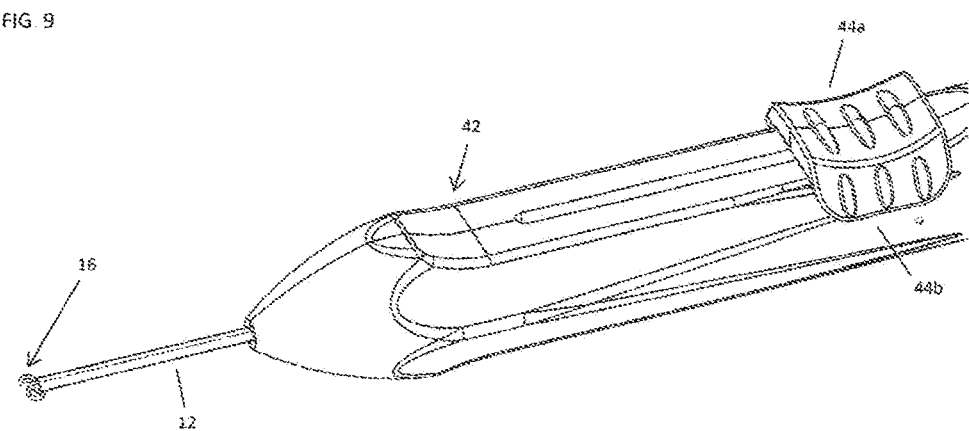
FIG. 9 is a perspective view of the surgical device of FIG. 8, with the sectioning elements in the first, insertion configuration.
Figure 15:
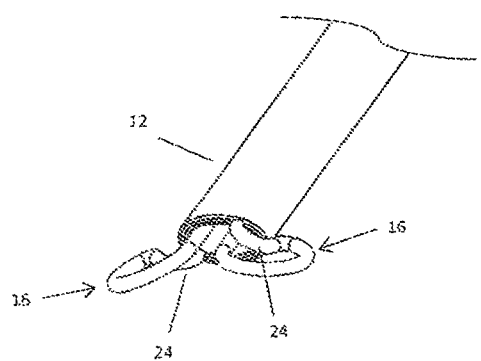
FIG. 15 is a detail perspective view of the distal end of the surgical device of FIG. 8.

Referring to FIGS. 8-9, one embodiment of the surgical device 40 includes two sectioning elements 16 extending from the distal end of a shaft 12, with a handle mechanism 42 attached to the proximal end of the shaft 12. Referring also to FIG. 15, two sectioning elements 16 are shown in the first, insertion configuration at the distal end of the shaft 12. The handle 42 has two sliders slidable longitudinally, which are connected to the two sectioning elements 16 as described below. The sliders in this initial configuration are in their retracted proximal location. The shaft 12 and sectioning elements 16 in the first, insertion configuration are inserted through an incision 4 in the cornea toward a capsulorhexis 10, as described above. As used in this document, the term "handle" includes both handles configured for manual gripping and actuation by a surgeon, as well as a robotic handle that is coupled to a surgical robot and configured for robotic control and actuation.

Figure 16:
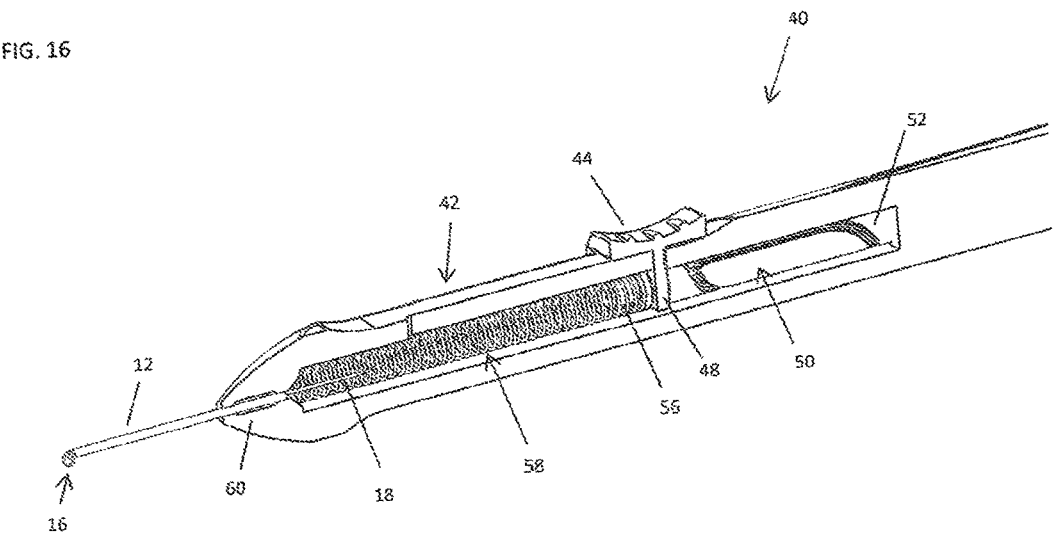
FIG. 16 is a cutaway perspective view of the handle, with the right slider in its initial position.
Figure 17:
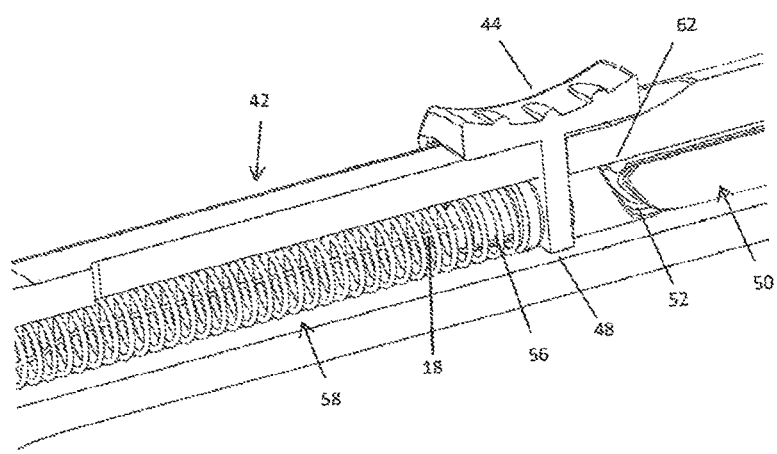
FIG. 17 is a detail perspective view of part of the handle of FIG. 16.

Referring also to FIGS. 16-17, one embodiment of a handle 42 of the surgical device 40 is shown in cutaway in a configuration corresponding to the first, insertion configuration of the sectioning elements 16. A slider 44 is slidable along the top surface of the handle 42. A finger 48 extends from the slider 44 into the handle 42 through a slot in the top surface of the handle 42. The finger 48 is coupled to a helical cam 50 or other cam structure, located proximal to the finger 48, that is longitudinally fixed to the finger 48 but that is free to rotate axially relative to the finger 48. This may be accomplished mechanically through an engagement pin, collar, or other suitable mechanism. A cam path 52 is defined in the surface of the helical cam 50. The helical cam 50 is confined within a chamber inside the handle 42 which allows the helical cam 50 to slide longitudinally but not move substantially radially. A nose 56 extends distally from the finger 48 and is rotatable relative to the finger 48. Advantageously the nose 56 is rotationally fixed to the helical cam 50; in some embodiments, the nose 56 is simply the distal end of the helical cam 50. A retraction spring 58 is positioned between the finger 48 and the front passage 60 out of the handle 42, acting to push the finger 48 toward the first, insertion configuration. The proximal end of the retraction spring 58 may be centered on and engage the nose 56. The proximal end of the first leg 18 of the sectioning element 16 may be fixed to the nose 16 in any suitable manner, such as by wrapping around the nose, friction fitting, welding, soldering, or by pressure fitting. Alternately, the proximal end of the first leg 18 may be fixed to the finger 48. A cam post 62 is defined in and/or fixed relative to the handle 42, and engages the cam path 52. As the helical cam 50 translates relative to the a remainder of the handle 42, the cam post 62 remains in the same place on the handle 42. Where two sectioning elements 16 are used, two such assemblies as described above (the slider 44, finger 48, cam 50, nose 56, retraction spring 58 and connection to the first leg 18 of the sectioning element 16) are utilized side-by-side within the handle 42. Such assemblies may be identical to one another, may be lateral mirror-images of one another, or may vary from one another in other ways that allow substantially the same assembly to operate two separate sectioning elements 16 in the manner described below. The description of the motion of the sliders 44a, 44b and the sectioning elements 16 are the same for both sliders 44 and sectioning elements 16 unless otherwise noted, and the descriptions of the two are interchangeable unless otherwise noted.

Figure 10:
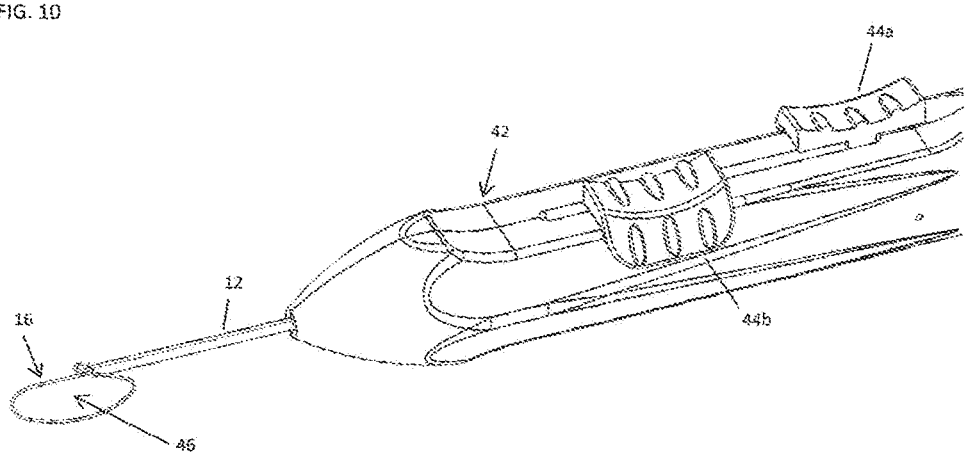
FIG. 10 is a perspective view of the surgical device of FIG. 8, with a left slider advanced to expand a left sectioning element toward the second, capture configuration.
Figure 18:
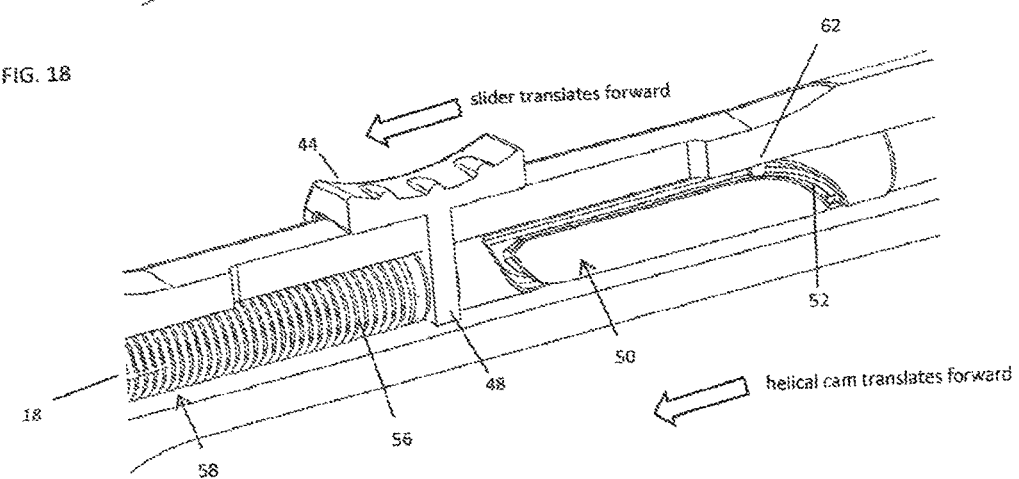
FIG. 18 is a detail perspective view of a different part of the handle of FIG. 16.

Referring to FIG. 10, one of the sectioning elements 16 is transitioned to the second, capture configuration by sliding the corresponding slider 44b distally One leg 20 of the sectioning element 16 may be connected to the shaft 12, handle 42, or other structure fixed relative to the handle 42, and maintained in a fixed position while the first leg 18 is configured to translate and rotate with the moving elements within the handle 42. As set forth above, the first leg 18 is attached to the nose 56. Referring also to FIG. 18, as the slider 44 translates distally, the finger 48 compresses the retraction spring 58, moves the nose 56 distally, and pulls the helical cam 50 distally. The retraction spring 58 is compressed and imparts a proximal force on the finger 48. If the user releases the slider 44, the slider 44, finger 48, and mechanisms translationally fixed to the finger 48 are pushed distally toward the initial position of the slider 44. As the slider 44 advances distally, the helical cam 50 translates within the handle 42. The cam path 52 may be substantially longitudinal during this first segment of motion of the slider 44, such that engagement between the cam path 52 and cam post 62 does not cause rotation of the helical cam 50; therefore, the sectioning element 16 remains in substantially the same rotational orientation relative to the longitudinal axis of the shaft 12. As the slider 44 advances distally, it pushes the first leg 18 of the sectioning element distally. As a result, the sectioning element 16 changes shape to the second, capture configuration, in the same manner as described above with regard to FIGS. 1-4.

Figure 11:
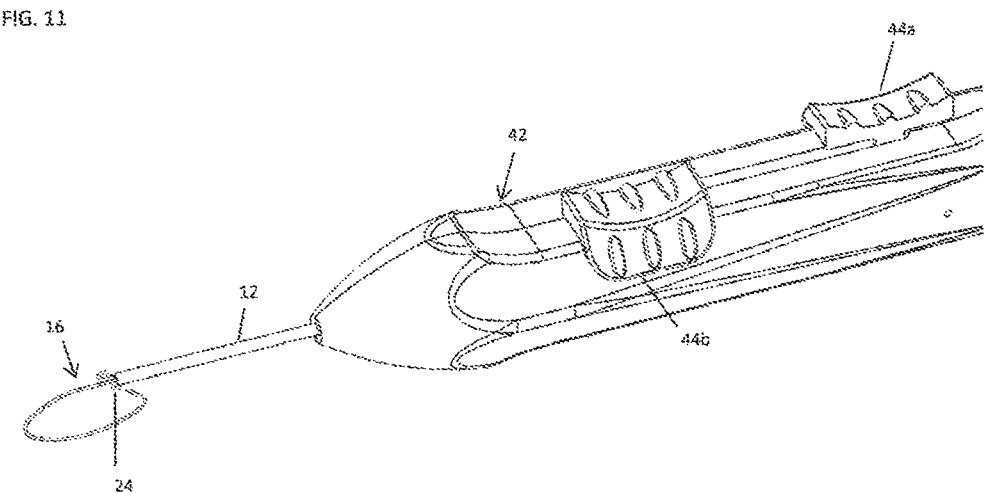
FIG. 11 is a perspective view of the surgical device of FIG. 8, with a left slider fully advanced to expand the left sectioning element to the second, capture configuration.
Figure 19:
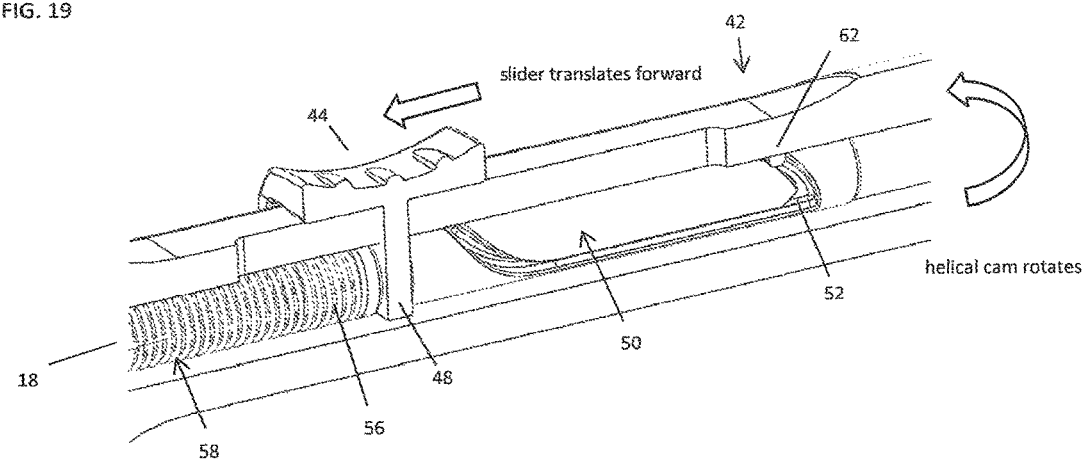
FIG. 19 is a detail perspective view of the handle of FIGS. 16-18, with the right slider partially advanced.
Figure 20:
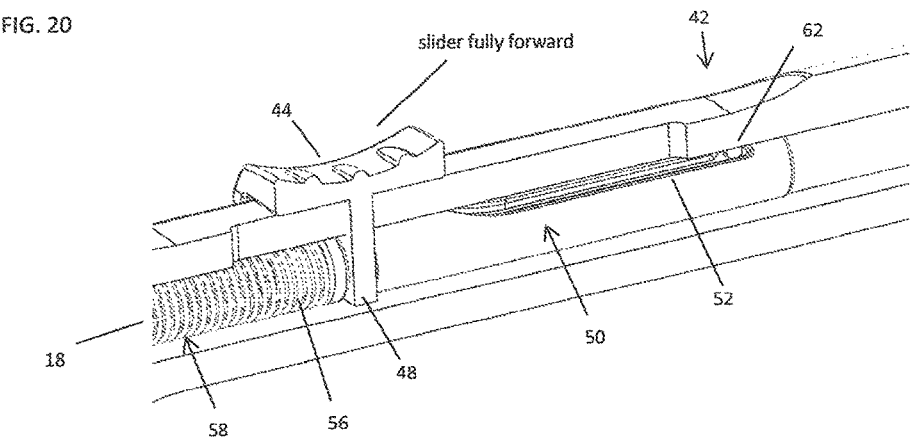
FIG. 20 is a detail perspective view of the handle of FIGS. 16-18, with the right slider advanced further distally than its position in FIG. 19.

Referring also to FIG. 11, the slider 44 may be further advanced distally after the sectioning element 16 changes shape to the second, capture configuration. The cam path 52 engages the cam post 62 to rotate the helical cam 50, as seen in FIGS. 18-20. The amount of distal motion of the slider 44 controls the amount of rotation of the helical cam 50. In this way, linear motion of the slider 4 is converted to rotary motion of the sectioning element 16. Because the helical cam 50 and the nose 56 are rotationally fixed to one another, rotation of the helical cam 50 causes rotation of the nose 56, and thus rotation of the sectioning element 16 in the second, capture configuration. The sectioning element 16 rotates, and the plane defined by the shape of the sectioning element 16 correspondingly rotates. The sectioning element 16 is rotated from its initial position, which may be substantially parallel to a plane defined by the edges of the capsulorhexis 10, to a position that is approximately within 0-40 degrees from a vertical orientation. During this rotation, the sectioning element 16 moves between the capsular bag 6 and the lens 8, capturing the lens 8 in the open area 46 within the perimeter of the sectioning element 16. The sectioning element 16 may not engage the capsular bag 6 and/or lens 8 substantially, or may be configured to engage either the lens 8 or the capsular bag 6. Alternately, the sectioning element 16 may cause a blunt dissection between the capsular bag 6 and the lens 8.

Referring also to FIG. 20, the slider 44 is moved fully forward and the rotation of the helical cam 50 and sectioning element 16 is complete. The sectioning element 16 surrounds the lens 8 within the capsular bag 6, and is configured to apply an inward cutting force relative to the lens 8, in the manner described above with regard to FIGS. 4-5.

Figure 12:
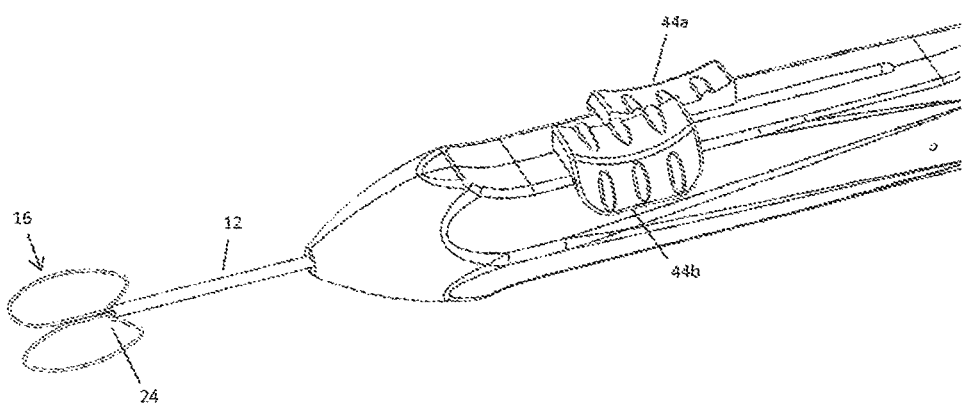
FIG. 12 is a perspective view of the surgical device of FIG. 8, with a right slider advanced to expand a right sectioning element toward the second, capture configuration.
Figure 13:
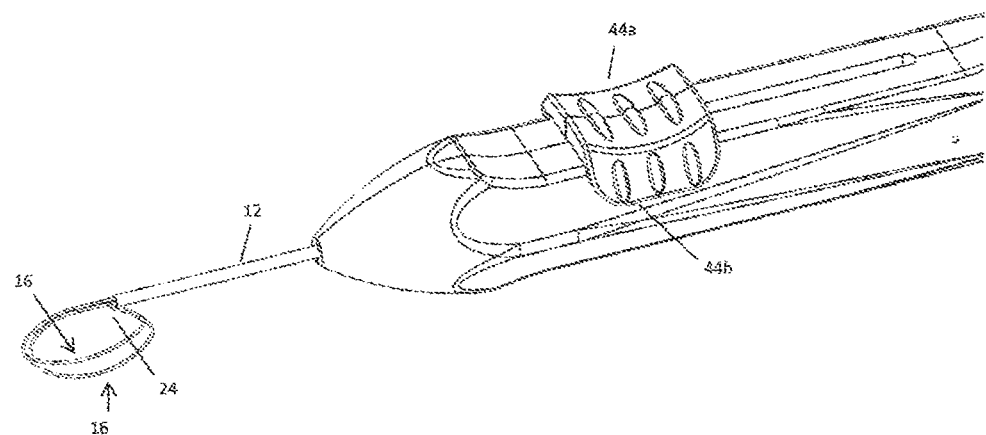
FIG. 13 is a perspective view of the surgical device of FIG. 8, with a right slider fully advanced to expand the right sectioning element to the second, capture configuration.
Figure 14:
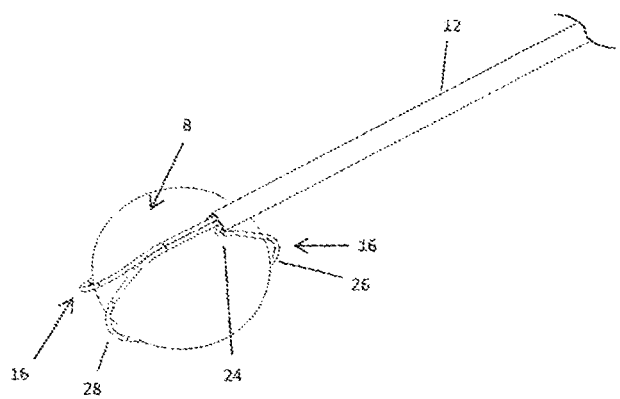
FIG. 14 is a perspective view of FIG. 13, showing the sectioning elements relative to the lens.
Figure 21:
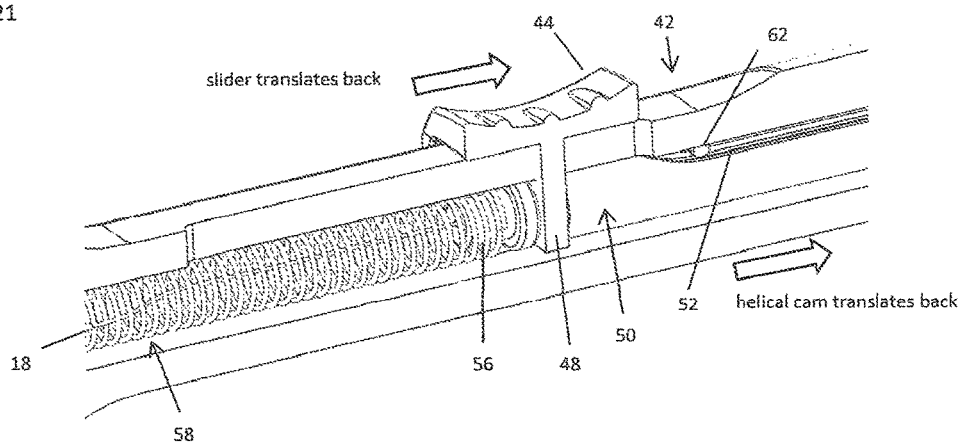
FIG. 21 is a detail perspective view of the handle of FIGS. 16-18, with the right slider returned toward its original position.

Referring also to FIGS. 12-13, a second sectioning element 16 then may be deployed to a second, capture configuration, and rotated into position to surround the lens 8, in the same manner as described above with regard to FIGS. 9-11 and 16-20. Referring also to FIG. 14, both sectioning elements 16 engage the lens 8, such that when the sectioning elements 16 are tensioned or otherwise closed, the sectioning elements 16 will cut the lens 8 into three partially- or fully-separate fragments. Referring also to FIG. 21, the tensioning may be provided by sliding the sliders 44 proximally, thereby pulling the first leg 18 of each sectioning element 16 proximally and tensioning it. In some embodiments, the proximal force exerted on the finger 48 by the retraction spring 58 may be sufficiently large to cut the lens 8 without the application of additional force by the user. In other embodiments, the user provides additional force that fragments the lens 8. This may be necessary especially for hard or difficult cataracts. Each sectioning element 16 engages the posterior surface of the lens 8 along a line spaced apart from the other sectioning element 16, and engages the anterior surface of the lens 8 along substantially the same line, according to some embodiments.

Figure 22:
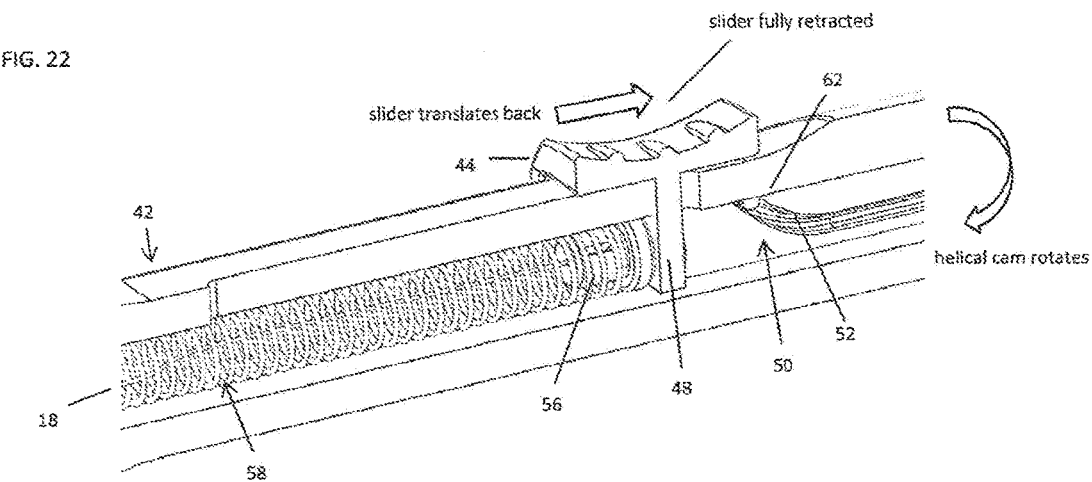
FIG. 22 is a detail perspective view of the handle of FIGS. 16-18, with the right slider returned to its original position.

In FIG. 22, the slider 44 is moved proximally to return to the original position. The sectioning element 16 is rotated back to its original plane of insertion, and then retracted toward the shaft 12. Referring also to FIG. 15, the sectioning elements 16 may return substantially to their initial configuration after sectioning the lens. The cam path 52 of the helical cam 50 may be a closed loop as shown. Alternately, the cam path 52 may be a one-way path wherein the slider 44 must be translated fully distally and then proximally to move it to the original position. In some embodiments, one-way latches or levers may be incorporated into the cam path 52 that prevent the helical cam 50 from rotating or moving in certain directions, and may be included at discrete positions of the cam path 52 or along the entire cam path 52.

According to some embodiments, the sectioning elements 16 may be configured to move synchronously with the actuation of a single slider 44, rather than each sectioning element 16 being coupled to a different slider 44a, 44b as described above. If so, the sectioning elements 16 may be configured to open and rotate at the same time. Alternately, the rotation of the sectioning elements 16 may be staggered such that one sectioning element 16 opens first and rotates first before the other sectioning element 16. This may be accomplished by associating a different cam path 52 and cam post 62 with each sectioning element 16. In still other embodiments, two sliders 44a, 44b can be configured such that a left slider 44b will move both sliders 44 forward but the right slider 44a will only move the right slider 44a forward (or vice versa). The right slider 44a may be configured to move both sliders 44a, 44b backward and the left slider to move only the left slider 44b backward. Thus, the user may decide whether to move the sliders 44a, 44b independently or synchronously.

According to some elements, the sectioning elements 16 are rotated in the same direction. For example, the first sectioning element 16 opens and is then rotated into the capsular bag 6 in a clockwise direction. The second sectioning element then opens and is also rotated into the capsular bag 6 in a clockwise direction. In this embodiment, the first sectioning element 16 may rotate to an angle 10-40 degree beyond a vertical plane, and the second sectioning element 16 may rotate to an angle 10-40 degree less than a vertical plane.

In still other embodiments, one or more additional or different mechanisms may be used to deploy the sectioning elements 16. For example, a scroll wheel advancing mechanism or other rotating mechanism could be used to deploy one or both sectioning elements 16. In some embodiments, the movement by the user is geared up or down to the movement of the sectioning element 16 such that moving a given amount of the user interface components moves the sectioning element 16 a greater or lesser amount through the use of gears, scaled pulleys or any other number of components. In some embodiments, certain parts of the surgical device 40 may be mechanically powered through components such as motors, linear motors, pneumatics, hydraulics, magnets, or the like. The surgical device 40 may be incorporated as a part of one or more larger robotic assemblies. For example, a robotic device which is configured to perform a cataract procedure may include an embodiment of the surgical device 40. This may allow surgeons to perform parts of the described method robotically. In some embodiments this may allow for alternate techniques and methods such as approaching the capsular bag 4 through the sclera. According to some embodiments, at least inserting a shaft 12 having a lumen 14 therethrough, through the corneal incision 4 toward the capsulorhexis 10, and extending a sectioning element 16 out of the distal end of the lumen 14, to cause the sectioning element 16 to bend away from the axis of the shaft 12 through the capsulorhexis 10, expand to a size greater than the capsulorhexis 10, and capture at least a part of the lens 8, are performed under robotic control.

In some embodiments, the sectioning element 16 need not approximate a loop initially as it is placed into the capsular bag 6. For example, the sectioning element 16 may be a single piece of round wire that is fed into the capsular bag 6 from the shaft 12, without doubling back on itself to form a loop. In such an embodiment, the distal tip of the sectioning element 16 is blunt to prevent puncture or damage to tissue within the eye 1. As the distal tip of the sectioning element 16 reaches the wall of the capsular bag 6, it may be configured to bend with either a predefined bend in its structure, or by tracking along the inner surface of the capsular bag 6. The sectioning element 16 may then traverse a sp ace between the lens 8 and the capsular bag 6 such that it goes around a circumference of the lens 8. The sectioning element 16 may then come back into the view of the user into the top portion of the capsular bag 6 where the user can grab the sectioning element 16 with features on the handle 42 such as grippers, or with a separate tool entirely. At this point, the sectioning element 16 surrounds the lens 8 within the capsular bag 6 and approximates a loop. As one or both ends of the sectioning element 16 are tensioned and/or pulled, an inward cutting force is applied to the lens 8 such that it is fragmented. The sectioning element 16 of this embodiment may have a cross-section that allows it to bend preferentially in certain directions more easily than others, such that the sectioning element 16 can bend as necessary to track around the lens 8 but still follow a suitable path around the lens 8 without going off track into tissue. This may include the use of a preferred bending moment cross-section like an "I" beam which bends preferentially about certain planes. Alternatively, a tube with cutouts to allow bending may be configured to bend in certain planes by placing the cuts in this plane. Therefore, the sectioning element 16 may bend around the lens 8, primarily in a distal-to-proximal manner. This may improve the ability of the sectioning element 16 to traverse a desired general path relative to capsular bag 6 and lens 8. In some embodiments, the sectioning element 16 may be entirely flexible such that its distal tip is unconstrained to travel in any predefined path. The distal tip may be configured to include a magnet or electromagnetic components to which a force can be applied to with an external electromagnetic field. An external device may then be used to control the location of the distal tip of the sectioning element 16 such that it may be guided around the capsular bag 6 along a desired path. Any number of different paths or fragmentation planes may be contemplated with this embodiment. The surgical device 40 may incorporate various imaging modalities in order to create a desired path for the distal tip of the sectioning element 16 which does not damage the capsular bag 6.

In some embodiments, the sectioning element 16 may bifurcate into multiple portions and/or multiple loops. For example, in the initial configuration, the sectioning element 16 may have a shape and profile as described above. However, when transitioned to the second, capture configuration, the sectioning element 16 may bifurcate along its length into two elements which may have the same or similar shapes, or different shapes, each surrounding the lens 8 in whole or in part. This may allow the sectioning element 16 to cut the lens 8 into multiple fragments without using two separate sectioning elements 16.

In some embodiments, one or both of the sectioning elements 16 may be configured to apply one or more types of energy to aid in the blunt dissection or fragmentation of the lens 8. For example, one or both of the sectioning elements 16 may include one or more portions configured to be heated through the use of electrically resistive wire that becomes hot as current is run through it. The increased temperature may improve the separation of the capsular bag 6 and the lens 8 as well as aid in sectioning the lens 8. Alternatively, any number of other modalities may be used such as radio frequency ablation, electric cautery, ultrasonic vibratory energy, or the like.

In some embodiments, the handle 42 may incorporate fluid delivery features. For example, as described above, the sectioning element 16 or the shaft 12 may allow the injection of fluids through the respective components. The handle 42 may include fluid passageways and paths that connect these components to external fluid sources through tubes, integrated connectors, or the like. Alternatively, the handle 42 may include internal pressure injection systems that push fluid through the shaft 12. The fluid may be stored in a cylinder with a piston wherein the piston is pressed forward by actuation components in the handle 42. For example, a separate slider or button may be connected to the piston and arranged such that as the slider is moved by the user, the piston is translated and expels a fluid from the cylinder into the injection system. This may allow the user to control the delivery of fluid through the sectioning element 16, the shaft 12, or any other handle 42 component at certain times during the procedure such as creating space between the capsular bag 6 and the lens 8. Alternatively, the surgical device 40 may be configured such that the fluid is injected automatically by the surgical device 40 during certain periods within the normal actuation of the device. For example, a spring may be configured to place a force on the piston such that as the helical cam 50 moves through its path, the piston is configured to expel an amount of fluid.

Figure 23:
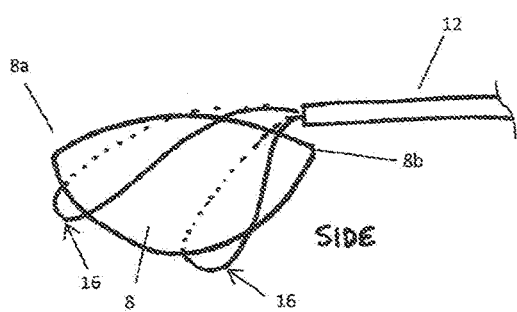
FIG. 23 is a side view of another embodiment of two sectioning elements extending from a shaft to encircle a lens.

Referring to FIG. 23, an alternate embodiment of sectioning elements 16 is shown as a side view. Two sectioning elements 16 extend from the distal end of the shaft 12. In this embodiment, the sectioning elements 16 are arranged to loop around the lens 8 starting at the distal end 8a of the lens 8, rather than around the sides of the lens 8 as described above. The sectioning elements 16 may be extended one at a time from the distal end of the shaft 12 distally toward the distal end 8a of the lens 8 and into the capsular bag. The sectioning element 16 may approximate a loop of wire which is configured to have a predefined shape and curves to allow it go around the lens 8 without placing excessive force on the capsular bag. This may include side-to-side bends as wells as forward-and-back curves that form various three-dimensional geometries as the sectioning element 16 is extended from the delivery device. In order to enter the capsular bag and capture the lens 8, the sectioning elements 16 are configured to be shaped differently as they expand. Rather than being planar, these sectioning elements 16 are curved downward from the shaft 12 in the second configuration, as seen in FIG. 23. Where multiple sectioning elements 16 are used, each may be configured to curve to a different degree than the other or others. One end of the sectioning element 16 may be extended while the other remains relatively fixed to the delivery device, or both ends may be extended at the same time, as described above. As described above, the sectioning element may have various profiles, materials, or flexibilities along its length.

One of the sectioning elements 16 may be extended to traverse the space between the capsular bag and the lens 8, and then may be moved downward and proximally around the lens 8. A second sectioning element 16 may be extended as shown, and any number of other sectioning elements 16 may be used. In some embodiments, a forward extending sectioning element 16 may be used in conjunction with a side extending sectioning element 16 as described above, in order to create intersecting fragmentation planes such that two sectioning elements 16 can slice the lens into 4 discrete pieces. Furthermore, the fragmentation planes can be at any number of angles to each other, and the sectioning elements 16 can extend around the lens 8 from any number of directions such as a combination of the forward extending and side extending embodiments.

Figure 24:
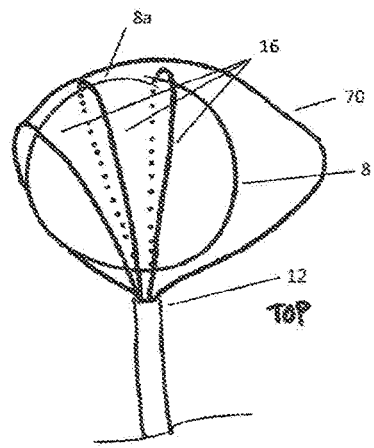
FIG. 24 is a top view of another embodiment of two sectioning elements extending from a shaft to encircle a lens, and a retention bag.

Referring to FIG. 24, another alternate embodiment is shown as a top view. In this embodiment, one of the sectioning elements 16 is attached to a retention bag 70 along at least a portion of its exposed length. The retention bag 70 may be fabricated from a thin polymeric material such as polyester, high density polyethylene, low density polyethylene, or any other suitable plastic. Alternatively, the retention bag may be comprised of a mesh like a small wire stainless steel braid, a nickel-titanium alloy braid, or any other suitable material. The retention bag 70 is connected to a portion of the sectioning element 16 and forms a cavity whereby the sectioning element 16 can change between an open and constricted configuration, which opens and closes the retention bag 70. In one embodiment, the sectioning element 16 with the retention bag 70 can be put into a constricted shape and placed into the eye 1 of the patient through the incision 4. The retention bag 70 may be concealed in the lumen 14 of the shaft 12 during insertion into the eye 1 through the incision. Then, the sectioning element 16 can be placed at the capsulorhexis 10 and inserted into the capsular bag 6 around the lens 8 as described above. In some embodiments, the retention bag 70 may have a predefined shape such as a profile of the lens 8 or a lens fragment. As the sectioning element 16 loops around the lens 8, the retention bag 70 follows the sectioning element 16, and the lens 8 enters into the cavity formed by the retention bag 70. The sectioning element 16 can be moved such that the entire lens 8 is scooped into the retention bag 70 all the way around the lens 8, according to some embodiments. The sectioning element 16 is then changed to a constricted shape that closes the retention bag 70 and encapsulates the lens 8. The retention bag 70 is then pulled out of the eye 1 through the incision 4. The lens 8 may fold and squeeze to pass through the corneal incision length 4 as it is removed. The retrieval bag 70 may be coated in any appropriate manner to enhance the ability to remove it out of the incision 4, such as by reducing the coefficient of friction of the retrieval bag 70. In other embodiments, additional tools or components may be used to fragment the lens 8 further, depending on the rigidity of the lens 8. For example, as shown in FIG. 24, multiple sectioning elements 16 may be inserted into the capsular bag to fragment the lens 8 within the retention bag 70. These additional sectioning elements 16 may be positioned at the same time as the retention bag 70 is positioned, or may be introduced after the retention bag 70 has removed the lens 8 from the capsular bag but before the lens 8 has been removed from the eye 1.

In other embodiments, other fragmenting modalities may be used once the lens 8 is within the retention bag 70. For example, once the lens 8 has been captured by the retention bag 70, ultrasonic energy or phacoemulsification may be used within the retention bag 70 to fragment the lens 8. This may include the use of telescoping probes into the retention bag 70 from the distal end of the shaft 12. Alternatively, mechanical instruments such as debriders, augers, or the like may be used to fragment the lens 8 sufficiently so that it may be pulled from the eye 1 through a narrow corneal incision 4.

In still other embodiments, the retention bag 70 described herein may be used as a retrieval device utilized after the lens 8 has been fragmented, in order to remove the lens fragments from the eye 1. For example, the device shown in FIG. 1 may be used to cut the lens 8 into any number of fragments. One or more of the fragments may be sufficiently large such that they are difficult to retrieve through the corneal incision with normal instrumentation. A retention bag 70 may be used to capture the lens fragments within the capsular bag or floating in the anterior chamber, and pull them out of the corneal incision 4. Additionally, the retention bag 70 may have cutouts or openings in it that allow the passage of fluid or small objects. For example, the retention bag 70 may be a mesh or a braid that allows aqueous humor fluid or viscoelastic fluid to permeate through the openings while still retaining the lens fragment.

Figure 25:
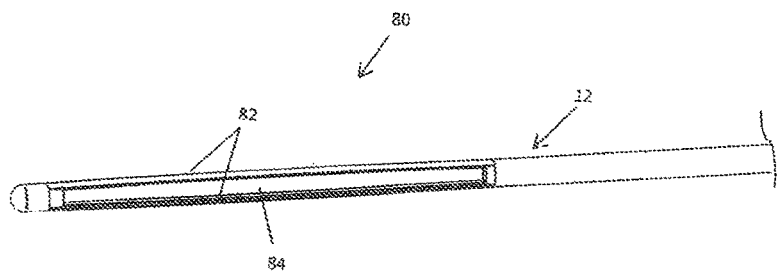
FIG. 25 is a perspective view of the distal end of another embodiment of a surgical instrument in a first, insertion configuration.

Referring to FIGS. 25-29, another embodiment of a surgical device 80 is shown for the removal of lens fragments 8f from the eye 1. The surgical device 80 includes an outer rotating element 82a and an inner rotating element 82b. The elements 82a, 82b are arranged concentrically along a central axis which may also define a longitudinal axis of the shaft 12. Referring to FIG. 25, the surgical device 80 is initially in a first configuration with the profile of the device small enough such that it can be inserted through a standard corneal incision 4, as shown in FIG. 1. The outer rotating element 82a and inner rotating element 82b may be tubes which have been cut along their length to produce straps 82 circumferentially separated by windows 84. The outer rotating element 82a may have an outer diameter which is appropriately sized to be able to fit into the corneal incision, ideally the outer diameter being between 0.015" and 0.060", although any outer diameter may be contemplated depending on the incision length targeted. The inner rotating element 82b may have an outer diameter which is sized to fit concentrically within the inner diameter of the outer rotating element 82a. The tubes of the outer rotating element 82a and inner rotating element 82b may be laser cut, machined, chemically etched, welded together, or manufactured with any suitable process in order to create the straps 82 and windows 84. The straps 82 may be sized to have any appropriate width that does not cut through the lens 8f when a force is applied to constrict the elements 82a, 82b, as described below. The width of the straps 82 may be between 0.004" to 0.050", although the straps 82 may have widths outside that range.

The outer rotating element 82a and inner rotating element 82b may be constricted to a second, capture configuration such as pushing the distal tip of the surgical device 80 forward with a separate component like a push rod, or by constraining the outer rotating element 82a with an additional outer tube which sheaths the surgical device 80 during insertion into the eye. Alternatively, the surgical device 80 is sufficiently flexible such that a constricting element is not required and the surgical device 80 flexes as it is inserted through the corneal incision 4. A distal tip 86 may be connected to the distal end of each of the outer rotating element 82a and inner rotating element 82b, and provides a smooth insertion into the corneal incision and blunt surface for contacting ocular structures. The distal tip 86 may be comprised of a soft polymer such as PEBAX® polyether block amide, polyurethane, thermoplastic elastomer, or the like. Alternatively, the distal tip 86 may be comprised of a hard material such a metal like stainless steel or titanium, or biocompatible nonmetallic substance. Alternately, the distal tip 86 may be sharp and allow the surgical device 80 to be inserted into the eye 1 without creating a previous incision 4, where the sharp distal tip 86 forms the incision. Where the outer rotating element 82a and inner rotating element 82b are composed of superelastic material, the transition from the first configuration to the second configuration may include a phase change of the material.

Advantageously, the straps 82 are configured to have a predefined open shape, such that once the surgical device 80 is within the anterior chamber of the eye 1. it is opened such that the elements return to their predefined shape. This may be accomplished using a shape memory material such as nickel-titanium alloy in its superelastic state, which is shaped to return to the open profile shown in FIG. 26 once a constricting element is released. Alternatively, the nickel-titanium alloy may return each strap 82 to an open shape once the device is inserted into the eye and allowed to heat to a body temperature which is above the transition temperature of the nickel-titanium alloy. Alternately, heating elements may be connected to the surgical device 80 to heat the surgical device 80 above an even higher transition temperature once the surgical device 80 is in a location where the open shape of the second configuration is desired. In other embodiments, the outer rotating element 82a and inner rotating element 82b may be comprised of any number of materials. For examples, elastic materials such as stainless steel, titanium, plastics, or the like may be used wherein the deformation is below the strain limit for elastic recovery. Alternatively, portions or the entirety of the straps 82 may be composed of multiple materials which may be additionally different from portions of the rotating elements 82a, 82b. For example, the straps 82 maybe fabricated from nickel-titanium alloy and affixed to rotating elements that are comprised of stainless steel. In the embodiments shown in FIGS. 25-29, each of the two rotating elements 82a, 82b includes two strap s 82. However, any other suitable number of straps 82 may be included as part of each rotating element 82a, 82b, and any suitable number of rotating elements 82a, 82b may be provided. For example, the device may include four rotating elements 82a, 82b stacked concentrically, with each containing only one strap 82. In this embodiment, the straps 82 may be rotated such that they are all grouped together, further reducing the crossing profile of the device at the corneal incision 4. In some embodiments, the predefined shape of the straps 82 is the initial configuration and the strap s are flexed outward to the second configuration.

Figure 26:
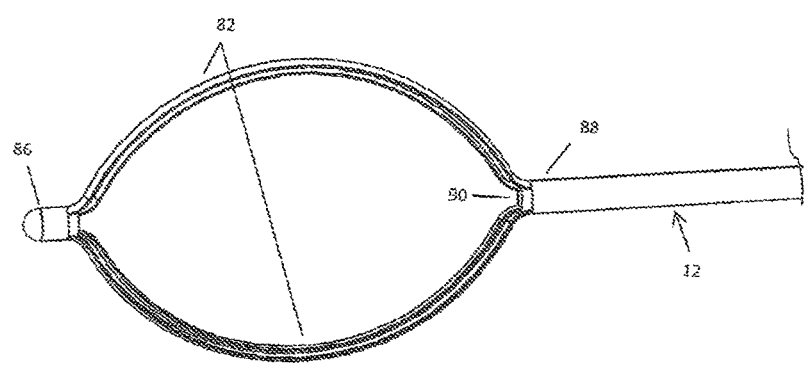
FIG. 26 is a perspective view of the distal end of the surgical instrument of FIG. 25, in a second, expanded configuration.
Figure 27:
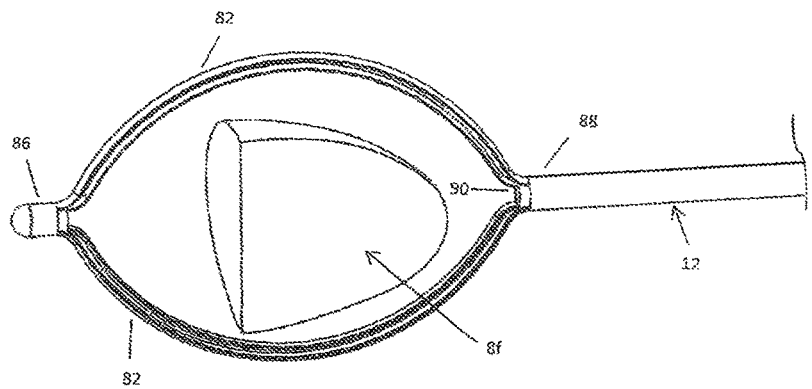
FIG. 27 is a perspective view of the distal end of the surgical instrument of FIG. 25, in a second, expanded configuration, encircling a lens fragment.
Figure 28:
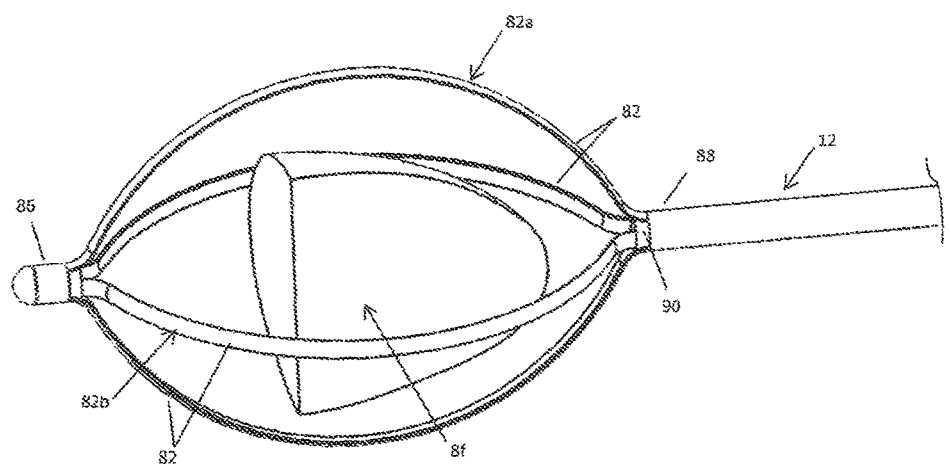
FIG. 28 is a perspective view of the distal end of the surgical instrument of FIG. 25, in a third, cage configuration.

Referring to FIG. 26, in the second configuration, the rotating elements 82a, 82b define a plane, and enclose a central area that is open in order to receive fragments of the lens may be looped by the device. Referring to FIG. 27, the surgical device 80 is moved to surround a lens fragment 8f. Referring to FIG. 28, the inner rotating element 82a and outer rotating element 82b have been rotated relative to one another approximately 90 degrees. The surgical device 80 is now in the third, rotated configuration. One or both of the rotating elements 82a, 82b may be rotated to achieve the third configuration. For example, a tube 88 attached to the proximal end of the outer rotating element 82b, and/or a tube 90 attached to the proximal end of the inner rotating element 82a, are rotated in order to rotated the rotating elements 82a, 82b to the third configuration. In other embodiments, the rotating elements 82a, 82b may be rotated to any other suitable angle relative to one another. In the third configuration, the inner rotating element 82a and outer rotating element 82b approximate a cage that surrounds the lens fragment 8f.

Figure 29:
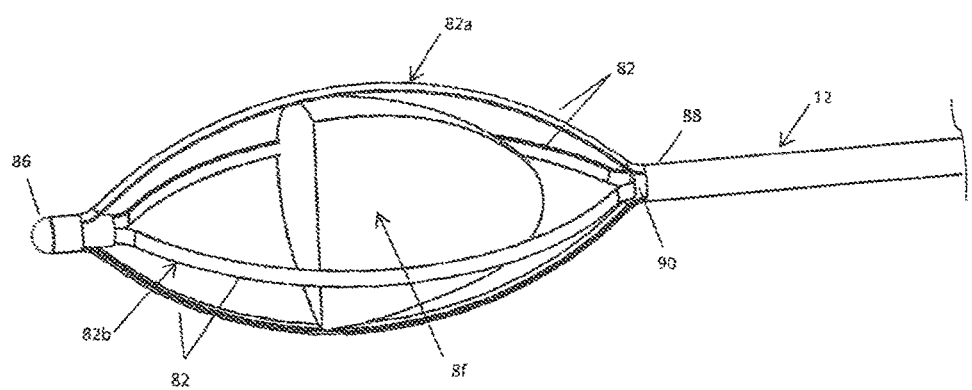
FIG. 29 is a perspective view of the distal end of the surgical instrument of FIG. 25, in a fourth, removal configuration.

Referring to FIG. 29, the straps 82 are moved to constrict around the lens fragment 8f. In some embodiments, a constricting element such as an outer sheath or a push and pull rod may be used to constrict the straps 82. In other embodiments, the mechanism or method to expand the straps to the second configuration is reversed. For example, where the straps 82 are superelastic, the straps 82 may be cooled or may be mechanically urged through a phase transition toward their initial shape. In other embodiments, the rotating elements 82a, 82b constrict as they are is pulled through the corneal incision 4. The incision 4 squeezes and compresses the straps 82 and the lens 8 such that the straps 82 and the lens 8 conform to the size of the incision 4 as they are pulled out. Additionally, other components and mechanisms may be incorporated to assist in removing the lens fragment 8f from the eye 1. For example, compression springs, pneumatic mechanisms, motorized mechanisms, and the like may be incorporated or used with the surgical device 80 to pull the lens fragments 8f from the eye 1. In some embodiments, the straps 82 may cut into the lens fragment 8f or additionally fragment the lens.

In some embodiments, the straps 82 may incorporate or be attached to removal bags as described above. A bag may exist between two or more 82 straps on one or more of the rotating elements 82a, 82b. In the open configuration, the lens fragment 8f is similarly able to be placed within the center area of the inner rotating element 82a and outer rotating element 82b. As the inner rotating element 82a and outer rotating element 82b are moved to the third configuration, the bag is likewise moved and captures the lens fragment.

In other embodiments, the device of FIGS. 25-29 may be constructed in any other suitable manner. For example, the rotating elements 82a, 82b may not be connected at their distal end and instead may form an open cage. In some embodiments, the rotating elements 82a, 82b may not be concentrically aligned or may be composed of non-tubular structures such as wires or beams or the like.

Figure 30:
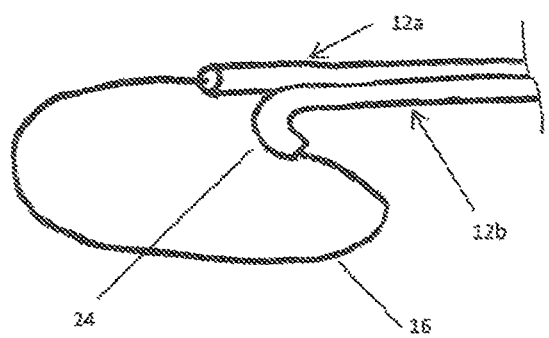
FIG. 30A is a side view of an alternate embodiment of a surgical instrument.
FIG. 30B is a side view of the device of FIG. 30A with inner tubes extending from both lumens.
Figure 30:
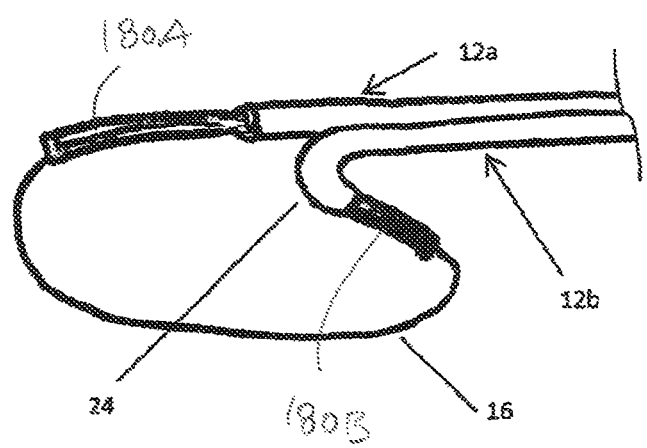

Referring to FIGS. 30A and 30B, an alternate embodiment is shown. Rather than a single lumen shaft 12, a two lumen shaft has a first delivery tube 12a and second delivery tube 12b. Each tube includes a lumen therethrough, and a sectioning element 16 extends through the free end of each delivery tube 12a, 12b to form the closed loop or shape. The sectioning element 16 may have the same characteristics as described above with regard to any of the embodiments. The second delivery tube 12b is bent back proximally (to the right as illustrated in FIG. 30), such that the proximal segment of the sectioning element 16 is able to rotate around a proximal end of the lens 8 in use. The free ends of the two delivery tubes 12a, 12b may be spaced apart from one another a distance that is less than the diameter of the capsulorhexis 10. Consequently, the delivery tubes 12a, 12b are able to deliver a flexible sectioning element 16 to the lens and provide for that sectioning element 16 to rotate relative to the lens 8 and surround at least part of the lens, as described above. The use of a simple flexible sectioning element 16, rather than a superelastic sectioning element 16, may simplify construction of the device. One or both of the delivery tubes 12a, 12b may be shaped in the same manner as at least part of a different embodiment of sectioning element 16 shown in FIG. 1; for example, the second delivery tube 12b may include the tight radius bend 24 that is made by the sectioning element 16 itself in the embodiment of FIG. 1. As described above, the sectioning element 16 may be expandable from a less-open initial shape to a more-open capture shape. For example, as an initial shape, the sectioning element 16 may extend substantially linearly between the ends of the delivery tubes 12a, 12b, after which an additional portion of the sectioning element 16 may be pushed out of the end of one or both delivery tubes 12a, 12b to form the curved, capture shape of FIG. 30. The embodiment of FIG. 30A is operated substantially as described above.

Referring to FIG. 30B, a first inner tube 180A is positioned in one of the lumens and a second inner tube 180B is positioned in the other lumen. The first and second inner tubes 180A, 180B may be used in any manner described in connection with the inner tubes described herein. The first and second inner tubes 180A, 180B may be advanced from both ends of the element 16 to shape the element 16, move the element 16 around the circumference, or any other use described herein. An advantage of the first and second tubes 180A, 180B is that they may be used to substantially shape the 16 so that the element 16 may be very flexible and advanced using the inner tubes 180A, 180B in a stepwise manner as described below.

In any of the embodiments above, vacuum suction may be incorporated into certain elements of the device 40, 80 such as the lumen 14 of the shaft 12, or the inner rotating element 82a. The vacuum suction may be used to aspirate small fragments of the lens or to hold a lens fragment in place during movement.

Figure 31:
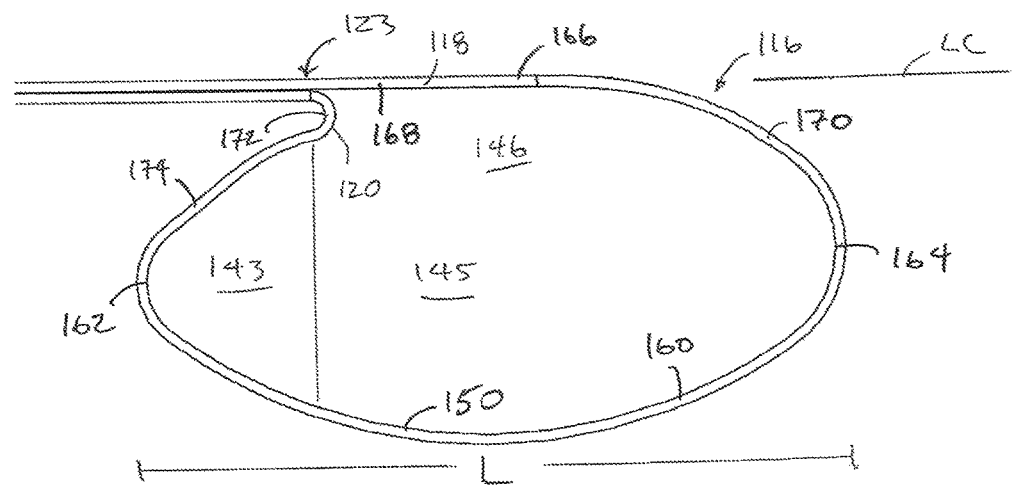
FIG. 31 shows another device for cutting a lens.
Figure 32:
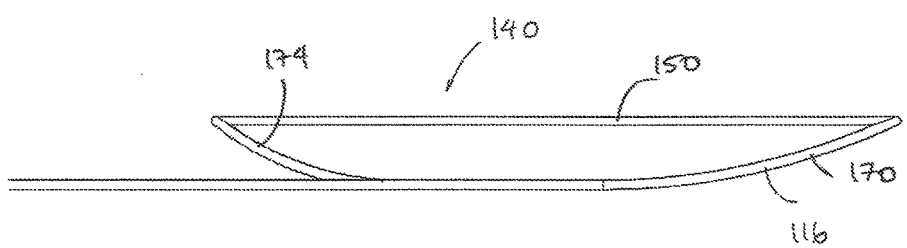
FIG. 32 is another view of the device of FIG. 31.
Figure 33:
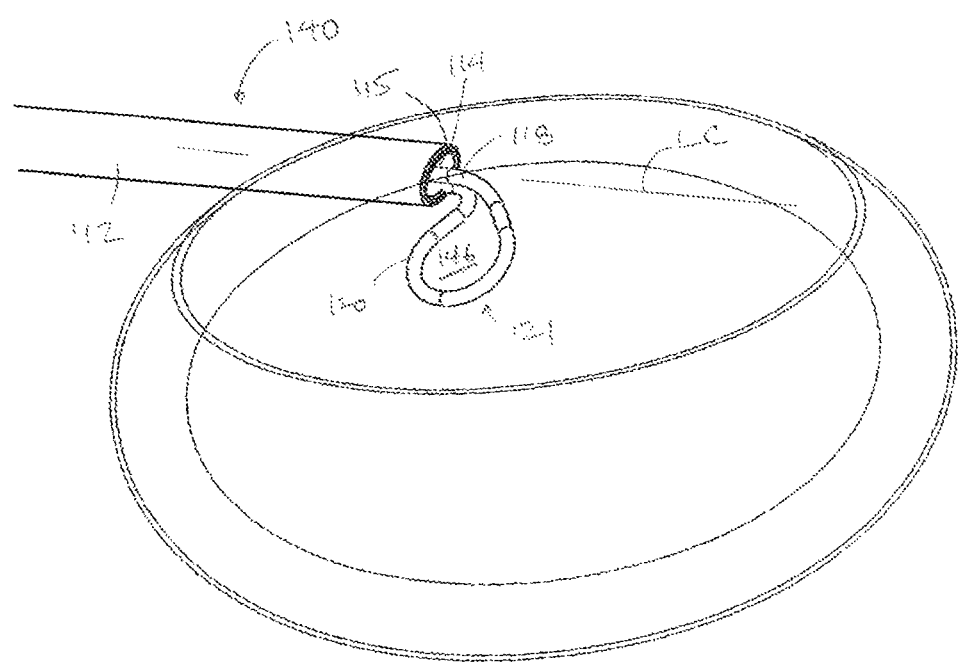
FIG. 33 shows the device of FIG. 31 with the element in a first configuration.
Figure 34:
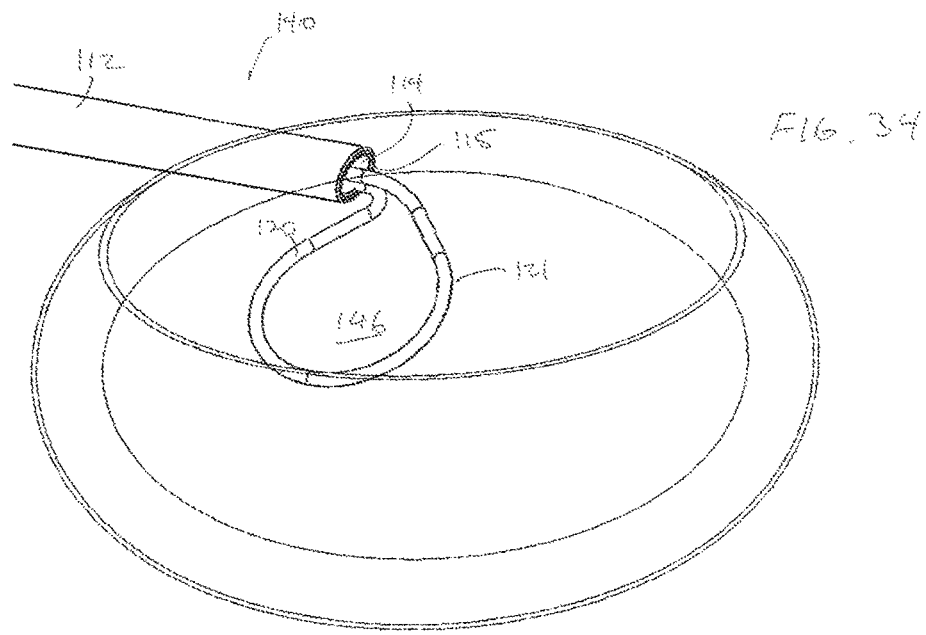
FIG. 34 shows the element extended further from the shaft.

Referring to FIGS. 31-33, another device 140 for cutting/segmenting a lens is shown. The device 140 has a cutting or sectioning element 116 which may be used in any manner described herein. Furthermore, all devices described herein may be used with any method described herein and all such methods are expressly incorporated for each device. The element 116 is movable from a first configuration shown in FIG. 33 to a second configuration shown in FIG. 31. The element 116 has a first leg 118 and a second leg 120. The first leg 118 may extend through a lumen 114 in a shaft 112 as shown in FIG. 33-36. The lumen 114 has an outlet 115 at a distal end 123 with the lumen 114 defining a longitudinal centerline LC at the outlet 115 which also generally defines the orientation of the element 16 as it exits the lumen 114. The shaft 112 may also have a second lumen (see FIG. 30) in which the second leg 120 is positioned so that both ends of the element 116 are slidable relative to the shaft 112 and manipulated as discussed herein. Alternatively, the second leg 120 may be coupled to the shaft 112 so that only the first leg 118 is slidable relative to the shaft 112.

The device 140 forms a closed loop 121 which increases in size as the element 116 moves from the first configuration to the second configuration. As described herein, the element 116 advances between the anterior surface of the lens and the capsular bag as the element 116 moves from the first configuration to the second configuration. The closed loop 121 forms an open area 146 defined by an orientation that maximizes the open area 146 of the closed loop 121. Once the device 140 is in the second configuration, the device 140 is manipulated to move the open area 146 around the lens to the desired location to cut the lens. The device 140 may also be used to dissect the posterior surface of the lens from the capsular bag by moving the element 116 as described above. The element 116 may be moved in any suitable manner such rotation of the element 116 and/or the shaft 112. The closed loop 121 may have a fixed size when moved such as during dissection. The closed loop 121 increases in size as the element 116 moves toward the second configuration with the closed loop 121 advancing between the lens and the capsular bag due to the increase in the size of the closed loop 121 and the elastic properties of the closed loop 121. The stiffness of the closed loop 121 requires a balance between providing a soft, pliable element 116 to reduce and prevent trauma to the capsular bag yet must also have sufficient stiffness to advance through the space between the capsular bag and anterior surface of the lens as the closed loop 121 expands. Traditional snares made of thin filaments are not capable of advancing in this manner since filaments cannot exert an outward force sufficient to advance between the lens and the capsular bag. A rigid loop, on the other hand, may be able to be advanced between the lens and capsular bag, however, an excessively rigid loop increases the likelihood of damaging the capsular bag.

The length of the element 116 that extends from the shaft 112 increases when the element 116 moves toward the second configuration. In one aspect of the invention, the first leg 118 may extend from the lumen of the shaft 112 for a first length which is at least 85%, or at least 95%, of a total length increase when the element 116 moves from the first configuration to the second configuration. Of course, when the second leg 120 is not movable relative to the shaft 112 the first leg 118 produces all of the length increase.

When the element 116 is in the first configuration of FIG. 33, a part of the element 116 may be positioned between the capsular bag and the anterior surface of the lens (capsular bag exaggerated for clarity) before moving the element 116 from the first configuration to the second configuration. For example, part or all of the closed loop 121 of FIG. 34 may be positioned or tucked between the capsular bag and lens prior to moving the element 116 to the second configuration. The element 116 may be positioned in the eye at a position above/anterior to the lens in any suitable manner. For example, the element 116 may be completely contained in the shaft 112 and extended from the shaft 112 into the first configuration of FIG. 34 after introduction into the eye. Alternatively, the element 116 may be in the first configuration when introduced into the eye and positioned over the lens in the first configuration. The element 116 may be advanced through another cannula or tube to contain the element during introduction into the eye. The device 140 may be introduced into the eye using any suitable access technique.

Figure 35:
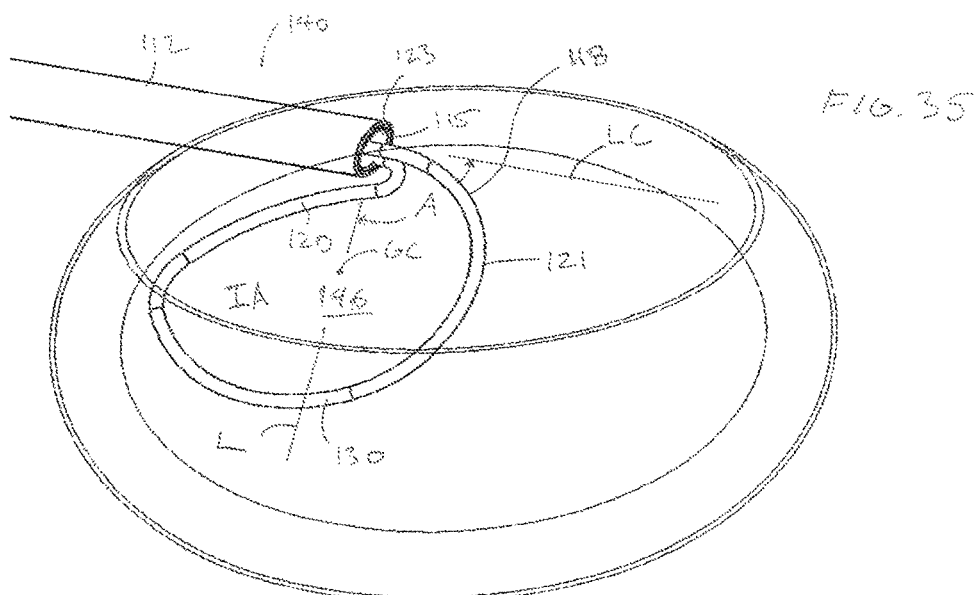
FIG. 35 shows the element in an intermediate position.
Figure 36:
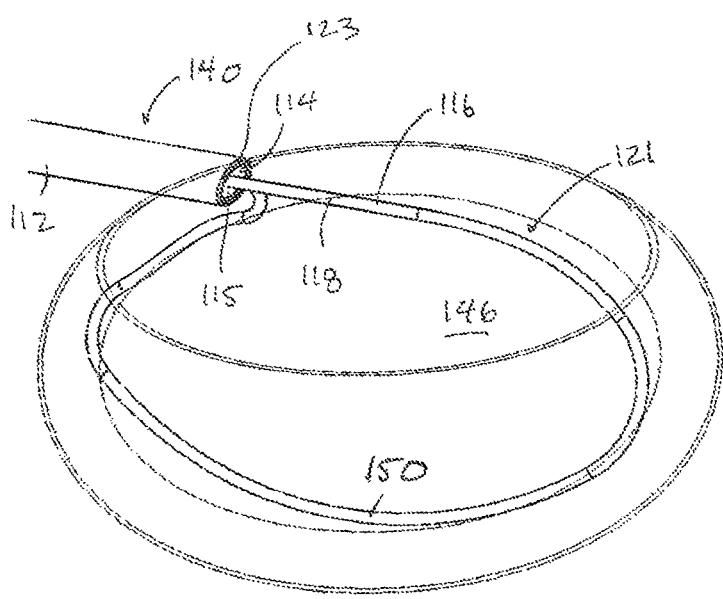
FIG. 36 shows the element in a second configuration.
Figure 37:
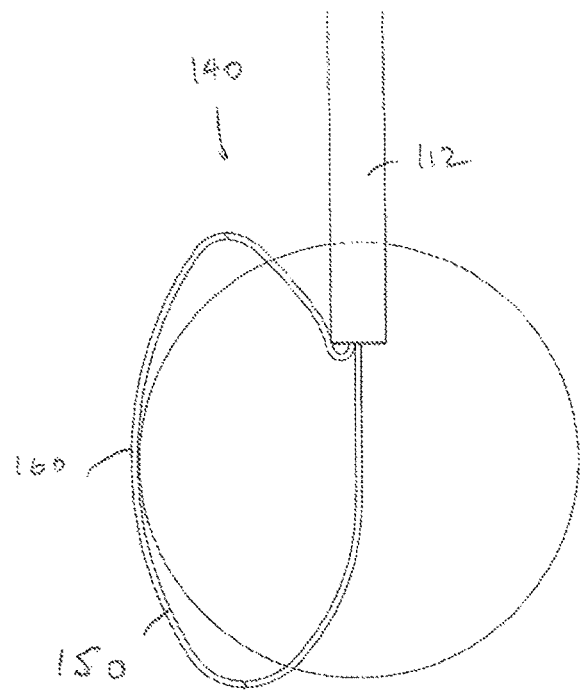
FIG. 37 shows the element in the second configuration positioned over the lens with the capsular bag removed for clarity.

The element 116 may form an intermediate position before reaching the second configuration as shown in FIG. 35. The device 140 forms an intermediate closed loop 130 in the intermediate position. The intermediate closed loop 130 has an area IA defined herein as 30% of the open area 146 in the second configuration. The intermediate position may alternatively be defined when a maximum dimension across the closed loop 121 reaches or equals 5 mm.

The intermediate position represents an intermediate state in which the closed loop 121 has reached, or nearly reached, the circumference of the lens. In accordance with the present invention, the element 116 extends from the lumen 114 in a manner that tends to spread the element 116 over the lens as opposed to pushing the closed loop 121 toward the capsular bag. The intermediate area IA formed by the open area 146 has a geometric center GC. The longitudinal centerline LC forms an angle A with a line L extending between the outlet 115 and the geometric center GC of at least 60 degrees, or at least 80 degrees. By orienting the element 116 and longitudinal centerline LC in this manner during the intermediate position, further extension of the element 116 from the intermediate position tends to spread the element 116 over the lens rather than moving the intermediate closed loop 121 toward the capsular wall as might occur with a small angle. Stated another way, the closed loop 121 and element 116 spread over the lens rather than protruding outwardly in that the second leg 120 displaces proximally relative to the distal end 123 of the shaft 112 when the element 116 moves to the intermediate position while the first leg 118 moves distally. Stated another way, the intermediate position has a proximal area PA positioned proximal to the distal end 123 of the shaft 112 which is at least 30% of the intermediate area IA.

Referring to FIG. 31, when the element 116 is in the second configuration the element 116 may extend primarily, such as at least 85%, or entirely, on one side of the longitudinal centerline LC which similarly enhances spreading of the closed loop 121. The open area 146 in the second configuration has a proximal portion 143 positioned proximal to the distal end 123 of the shaft 112 and a distal portion 145 positioned distal to the distal end 123 of the shaft 112. The position of the distal end 123 of the shaft 112 (not shown) is indicated in FIG. 31 for clarity. The proximal portion 143 has an area which is at least 10% of the open area 146 in the second configuration. Stated another way, at least 10% of a length L of the element 116 is positioned proximal to the distal end 123 of the shaft 112 in the second configuration with the length being measured along longitudinal centerline LC.

The element 116 may also have an advancing portion 150 which moves toward the circumference of the lens when the element 116 moves from the first configuration to the second configuration. The advancing portion 150 has a section 152 that flips in unison to a posterior side of the lens. The advancing portion 150 may have a radius of curvature in the second configuration which is greater, such as 20% or 40% greater, than a radius of curvature of the circumference of the lens. The larger radius of curvature along the advancing portion 150 may help prevent the element 116 from protruding excessively into the capsular bag as might occur with more curved shape. The advancing portion 150 may have a variable radius of curvature, of course, without departing from the scope of the invention. As used herein a straight section shall be deemed to have an infinite radius of curvature and therefore larger than the lens radius for the purposes of definition herein.

The section 152 of the advancing portion 150 that flips around the circumference moves to a position between the posterior surface of the lens and the capsular bag rather than extending outwardly after moving around the circumference. The section may flip around the circumference of the lens due to the element 116 simply moving to the second configuration without requiring additional manipulation of the element 116 (such as rotating the element 116 and/or shaft 112). Alternatively, the device 140 may be manipulated to flip the section 152 to the posterior side of the lens during or after moving the element 116 to the second configuration.

The section 152 may have a critical length that flips to the posterior side of the lens. In one aspect, the section 152 flips to the posterior side with the critical length being at least 2 mm, or at least 4 mm, when the circumference of the lens has a 5 mm radius. The section 152 of the advancing portion 150 that flips to the posterior side of the lens forms an angle of at least 20 degrees, or at least 45 degrees, with an axis 154 of the lens. The advancing portion 150 may also have a length of at least 6 mm.

The advancing portion 150 also defines an envelope 156 in the second configuration which bounds the element 116 so that no parts of the element 116 extend beyond the envelope 156. The envelope 156 is defined by a symmetrical extension of the advancing portion 150 to an angle of 180 degrees. The element 116 may be positioned entirely within the envelope 156 in the second configuration. The advancing portion 150 may be the first part of the element 116 to reach the circumference of the lens when viewed along the axis 154 of the lens. The open area 146 in the second configuration may have a width in a direction transverse to the longitudinal centerline that is no more than 0.7 times a radius of curvature of the advancing portion 150. The advancing portion 150 may also have a length which is at least 25% of the length L of the element 116 in the second configuration (see FIG. 31). The advancing portion 150 may also be positioned on a posterior portion 160 of the element 116 when the lens is positioned in the open area 146 prior to cutting the lens. The posterior portion 160 has a posterior length PL and the advancing portion 150 has a length which is at least 70% of the posterior length PL.

The device 140 is now described in further detail with reference to FIGS. 31 and 32. The posterior portion 160 of the element 116 includes about half of a proximal bend 162 and about half of a distal bend 164. The proximal bend 162 and the distal bends 164 are positioned adjacent the circumference of the lens and each bend 162, 164 straddles the anterior and posterior sides of the lens. An anterior portion 166 of the element 116 has a straight segment 168 extending from the lumen 114 of the shaft 112 and leading to a distal curve 170. The distal curve 170 has a radius of curvature of 0.2143 in, the proximal bend radius is 0.0394 in, the distal bend radius is 0.0689 in, the advancing portion 150 radius is 0.3176 in and a tight bend 172 radius is 0.0059 in. The tight bend 172 may have any of the features described herein for the tight bend radius such as the angle being at least 120 degrees. Referring to FIG. 32, the distal curve 170 and a proximal curve 174 are both curved with the distal curve having a radius of 0.414 in and the proximal curve having a radius of 0.186 in. The element 116 may be a nitinol wire with the shape set as described above although other cross-sections and shapes may be used without departing from numerous aspects of the invention. The wire may have a diameter of 0.004 in to 0.008 in. although other sizes may be used and the size and cross-section vary without departing from the scope of the invention. The element 116 has a concave shape as shown in FIG. 32 which faces the convex anterior surface of the lens to encourage the element 116 to advance smoothly between the convex anterior surface of the lens and the capsular bag.

The device 140 and other devices described herein may be designed to advance gently between the lens and capsular bag due primarily to elastic expansion of the closed loop. To this end, the closed loop being in a collapsed condition which is smaller than an unbiased shape of the closed loop when the element is extended. The closed loop expands toward the unbiased shape as more of the element extends from the shaft which naturally advances the loop between the capsular bag and the lens. The unbiased shape of the closed loop is larger than the intermediate shape and may be the closed loop shape formed when the element is in the second configuration. Of course, the unbiased shape may be smaller or larger than the second configuration without departing from numerous aspects of the invention. Stated another way, the closed loop formed by the device advances between the capsular bag and lens due to natural expansion of the closed loop. The length of the element extending from the lumen increasing to increase the size of the closed loop.

Figure 40:
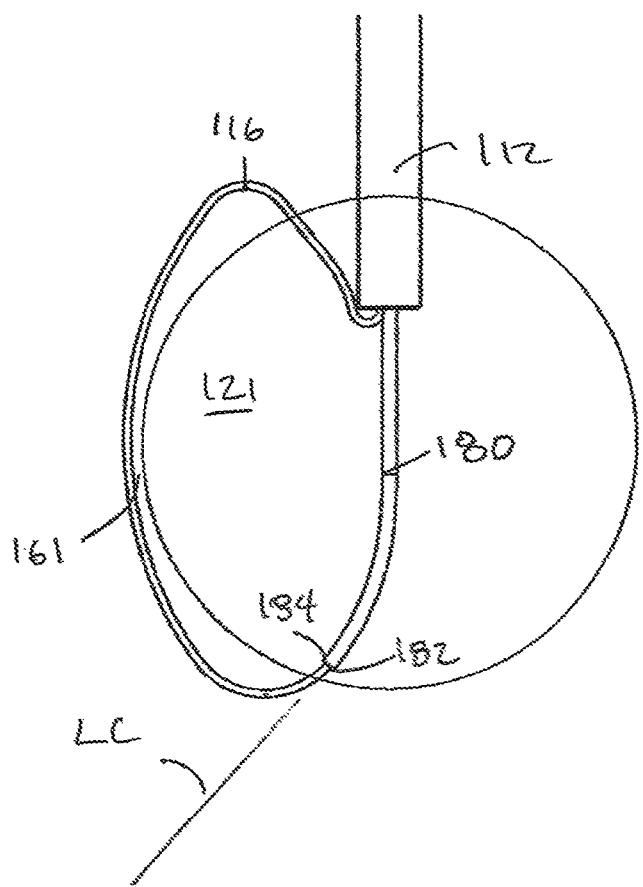
FIG. 40 shows an inner tube extended over the element to change the shape of the element.

Referring now to FIG. 40, the device 140 is shown with the shaft 112 having an inner tube 180. The inner tube 180 is positioned in the lumen 114 and is slidable within the lumen 114 and movable to an extended position with the inner tube 180 extending from the outlet 115 of the lumen 114. The inner tube 180 has a tube lumen 182 and a tube outlet 184 through which the element 116 extends. This inner tube 180 may be adapted to work in conjunction with other embodiments described herein such as demonstrated in FIG. 30. In particular if inner tube 180 was slidable within tube 12a it would be possible to make wire 16 from a much more flaccid material such as suture or thinner metal wire and still achieve the described lens encapsulation.

Figure 38:
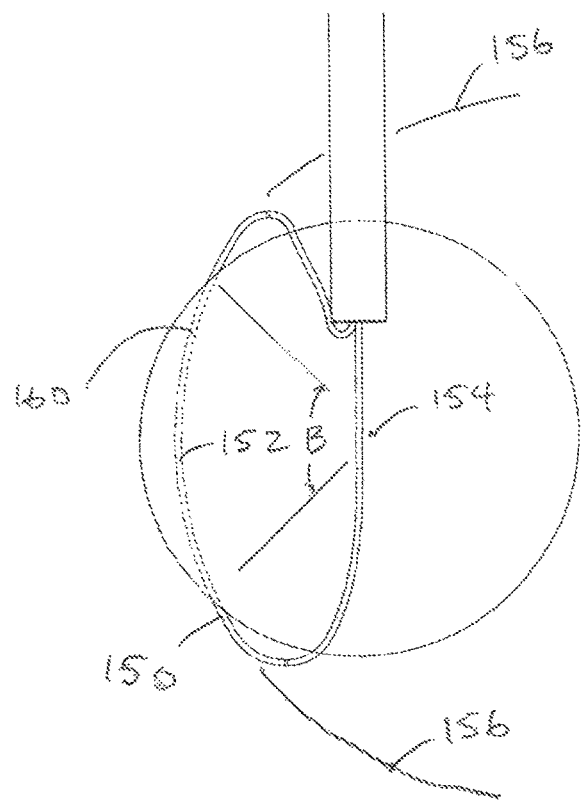
FIG. 38 shows a section of the element that has passed around the circumference of the lens to a position posterior to the lens.

The inner tube 180 may be advanced over the element 116 to change the shape of the element 116 and the closed loop 121 as shown in FIG. 40. For example, the inner tube 180 may have a shape that curves posteriorly as the inner tube 180 moves out of the lumen. The inner tube 180 may change the shape of the element 116 to flip the section 160 (see FIG. 38) around the circumference as described above. FIG. 40 depicts a small separation 161 between the element 116 and the lens which would permit the section 160 of the closed loop 121 (and in particular the advancing portion) to move to the posterior side of the lens as shown in FIG. 38. As such, the inner tube 180 may be advanced over the element 116 to move the section of the closed loop 121 to a posterior side of the lens. The inner tube 180 may be advanced in steps and may be coordinated with stepwise extension of the element 116 and expansion of the closed loop 121. For example, the element 116 may be extended to expand the closed loop 121 with the inner tube 180 being advanced in two steps; one before and one after extension of the element 116.

Figure 39:
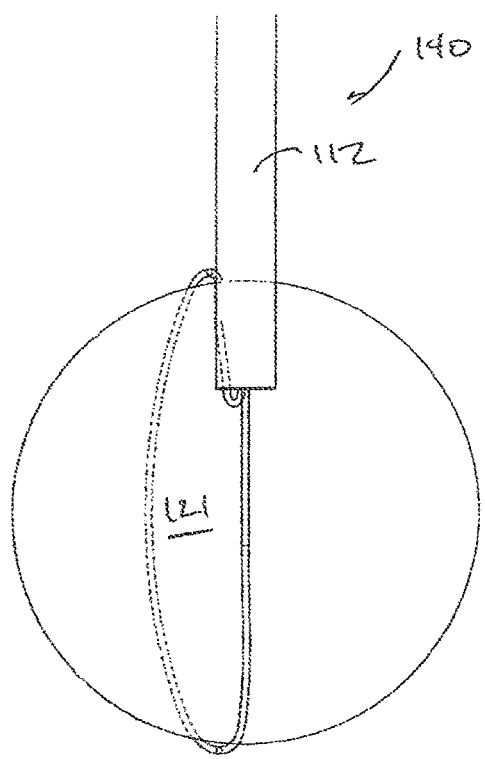
FIG. 39 shows the element rotated so that the lens moves through the closed loop.

In another method of using the inner tube 180, the element 116 may be extended from the shaft 112 to increase the exposed length and the size of the closed loop 121 by retracing the shaft 112 relative to the inner tube 180 so that the closed loop 121 spreads proximally. All applicable aspects of the invention, such as those related to encouraging spreading of the closed loop 121 over the lens, are equally applicable here as mentioned above. The element 116 has a first end extending from the inner tube 180 outlet and a second end attached to the shaft 112. The inner tube 180 may also help to move the element 116 so that the lens moves through the closed loop 121. Stated another way, the element 116 is moved so that the closed loop 121 sweeps around a portion of the anterior surface and the posterior surface of the lens. For example, the element 116 may be rotated to dissect the posterior surface of the lens from the capsular bag into the position of FIG. 39. When the shaft 112 includes the inner tube 180, as used herein the outlet of the shaft 112 and the longitudinal centerline LC of the shaft 112 shall be defined by the more distal of the lumen outlet 115 and the inner tube outlet 184 since the element 116 is free from constraint when exiting the distalmost outlet. Stated another way, the inner tube outlet 184 constitutes the outlet of the shaft 112 and defines the longitudinal centerline LC when the inner tube 180 extends from the lumen 114 of the shaft 112.

Figure 45:
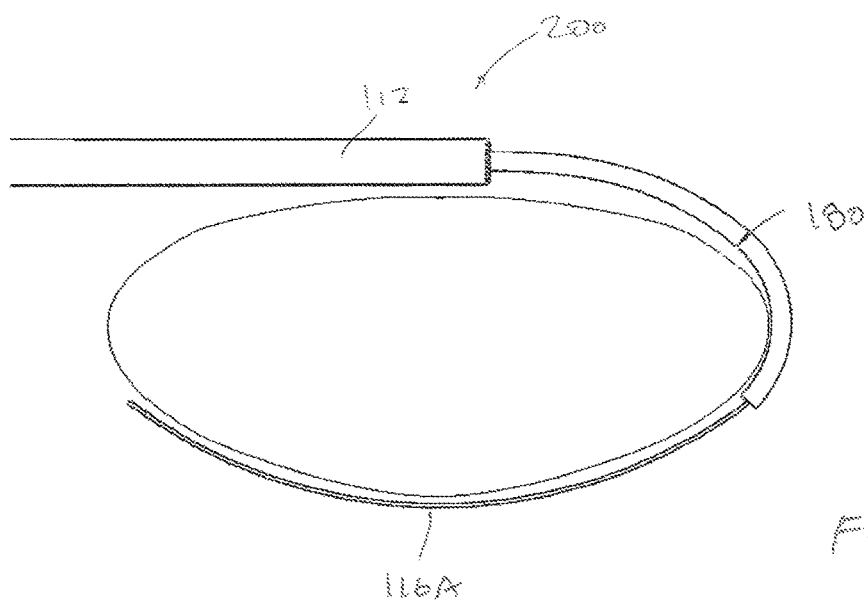
FIG. 45 shows the element extending further from the inner tube around the posterior side of the lens.
Figure 46:
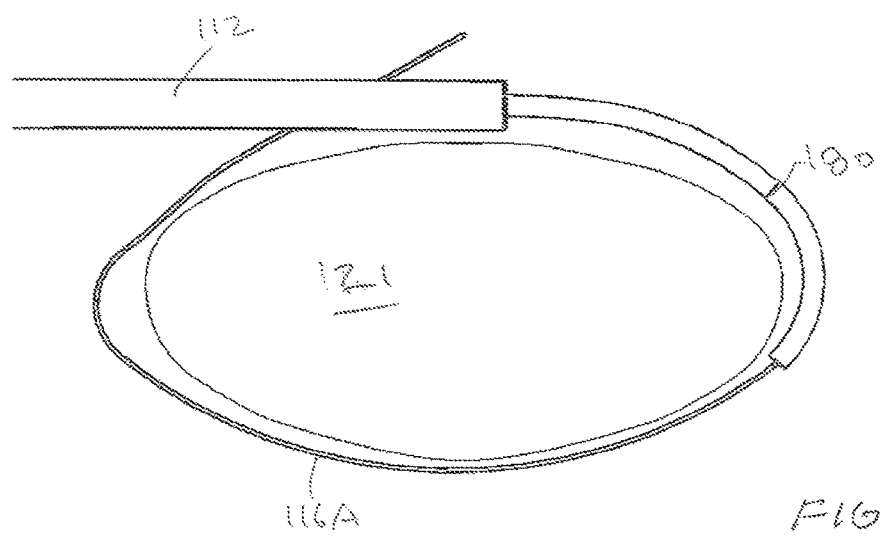
FIG. 46 shows the element extended around the lens.
Figure 47:
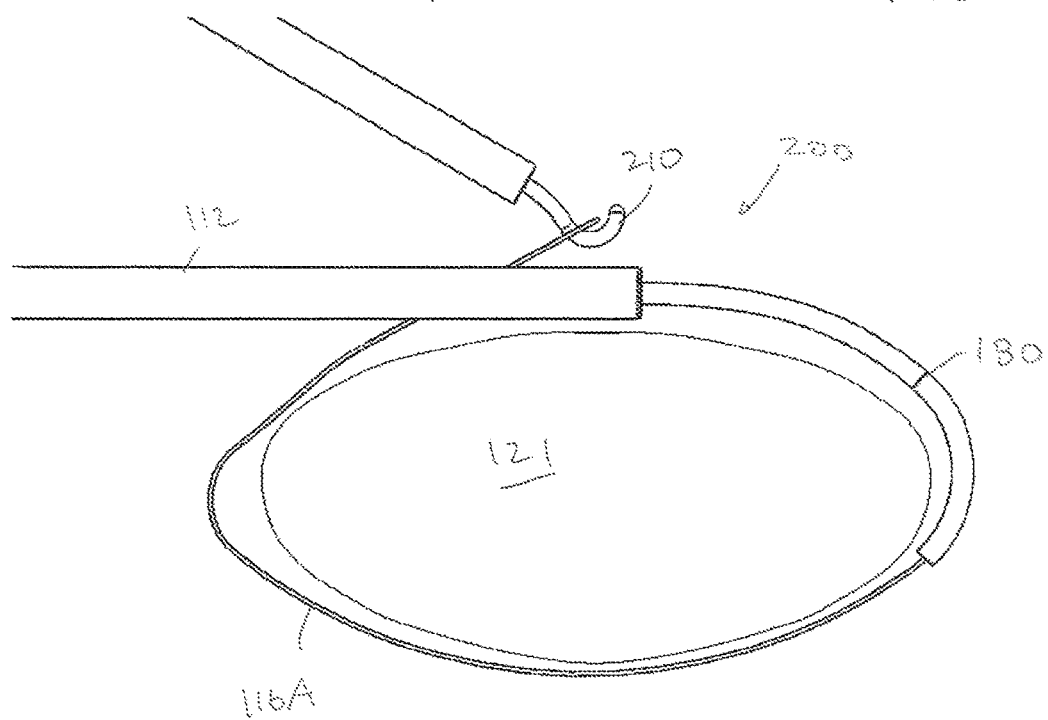
FIG. 47 shows the element engaged to form a loop.
Figure 48:
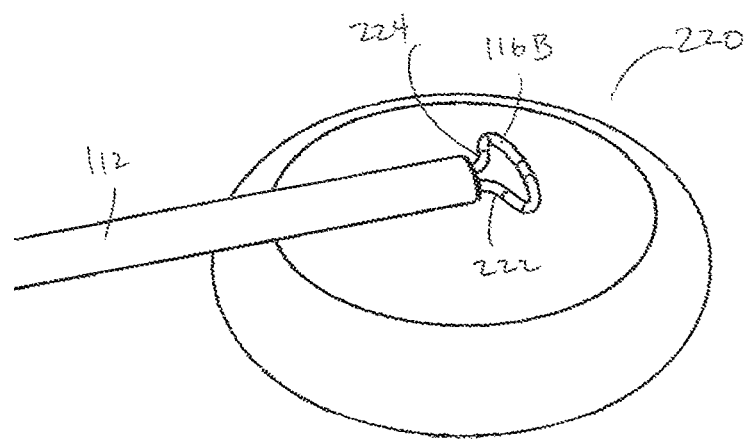
FIG. 48 shows another device for cutting a lens within a capsular bag.
Figure 49:
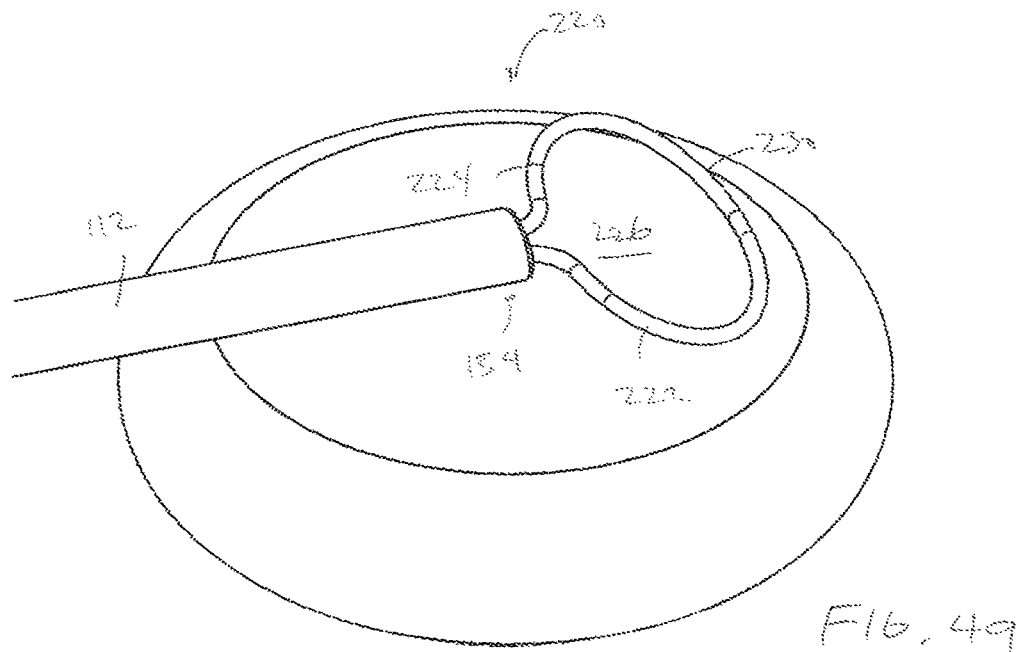
FIG. 49 shows the device of FIG. 48 with the closed loop expanded.
Figure 50:
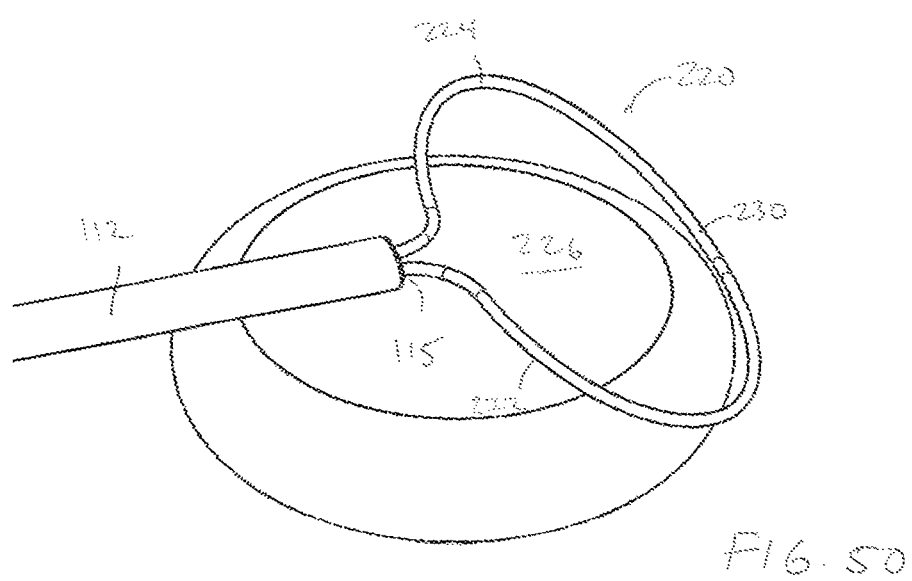
FIG. 50 shows the device of FIG. 48 with the closed loop expanded further.
Figure 51:
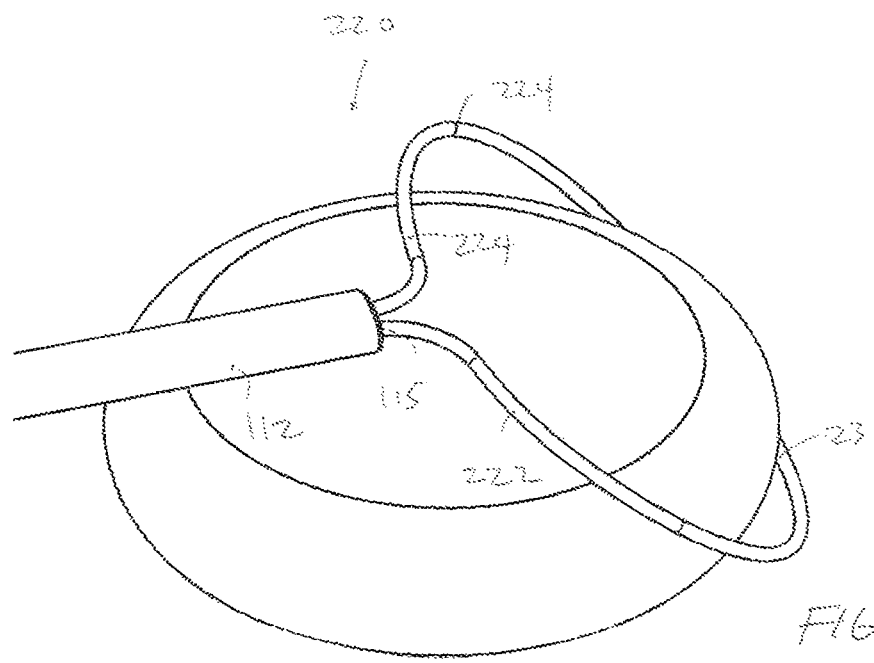
FIG. 51 shows the device of FIG. 48 with the closed loop expanded to move around the circumference to the posterior side of the lens.
Figure 52:
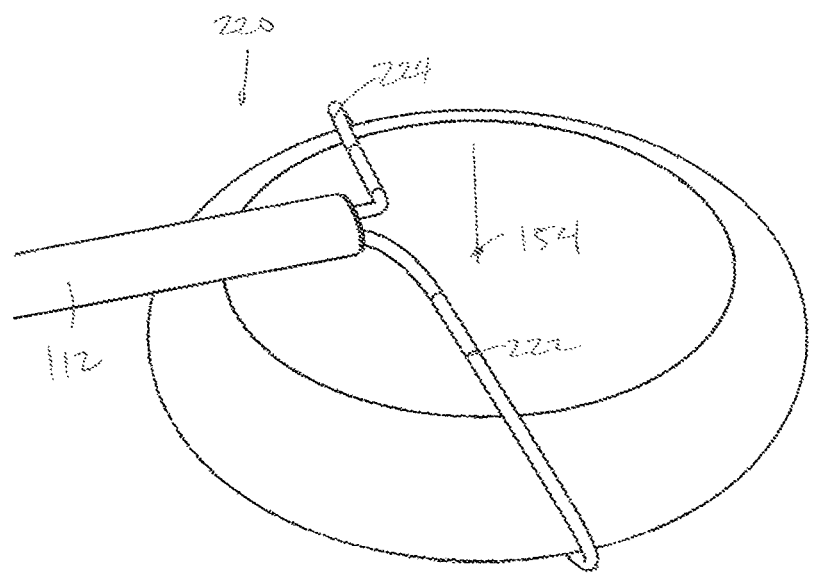
FIG. 52 shows the device of FIG. 48 with the closed loop expanded and positioned to form a cut in the lens.

Referring to FIGS. 41-47, another device 200 for cutting a lens within a capsular bag is shown. The device 200 includes an element 116A having a distal end 202 which may be a free end. The element 116A is extended around the lens and a location on the element 116, such as the distal end 202, is engaged as shown in FIG. 47. The element 116A is then tensioned so that the lens is positioned in a loop 121A which decreases in size to cut the lens. The element 116A has a coupling which is engaged to apply tension to the element 116A. The coupling may be any suitable coupling such as an eyelet 208 which may be engaged by a hook 210. Any other suitable engaging element, such as graspers or snare, may be used. Furthermore, the engaging element may be coupled to the shaft or independent of the shaft. The element 116A may also be grasped with a slot or tab on the shaft 112 or inner tube 180. Tension may be applied to the element 116A in any suitable manner including pulling on one or both ends of the element 116A or by cinching the shaft 112, inner tube 180 or any other suitable structure over the element 116A (while holding the element 116A stationary) or any combination thereof.

Figure 41:
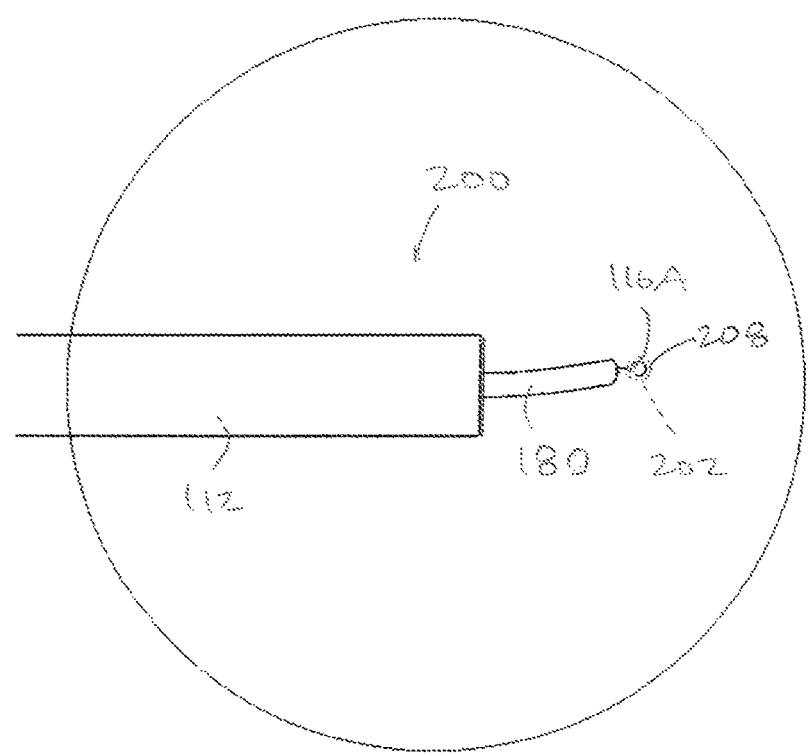
FIG. 41 shows another device for cutting a lens positioned over the lens with the capsular bag removed for clarity.
Figure 42:
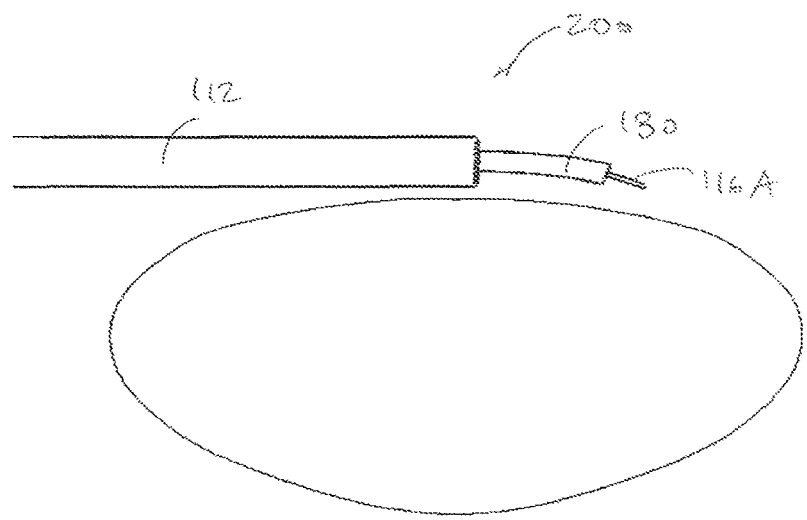
FIG. 42 shows the device of FIG. 41 in another view.
Figure 43:
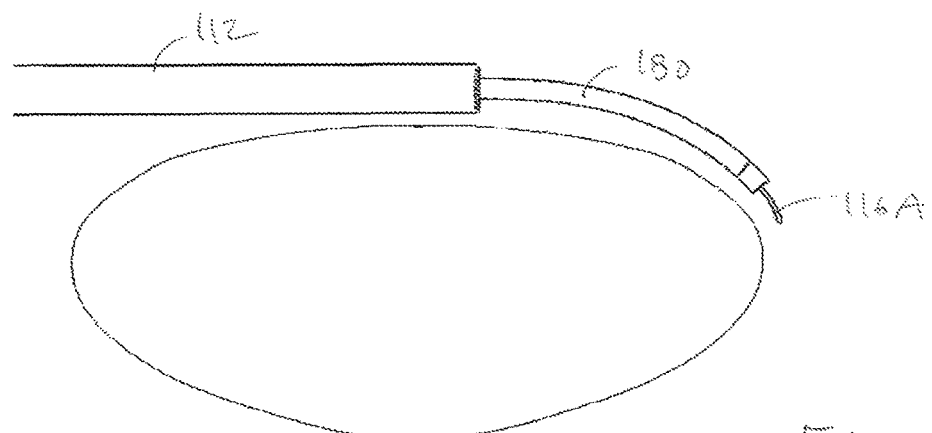
FIG. 43 shows the inner tube curved posteriorly.
Figure 44:
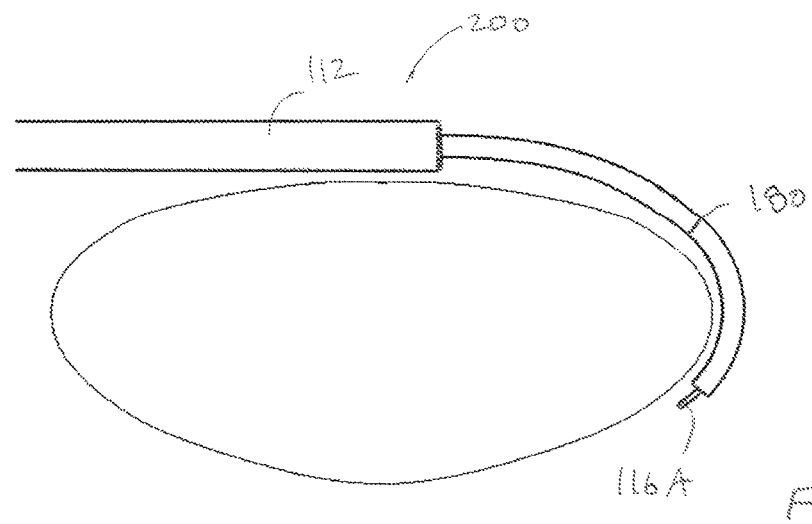
FIG. 44 shows the inner tube extending around the circumference of the lens.

The element 116A is positioned in the shaft 112 which may include the inner tube 180 as well. FIGS. 41 and 42 shows the shaft 112 positioned adjacent to a lens within a capsular bag with the element 116A and inner tube 180 both extended from the outlet 115 in the lumen 114. The element 116A may be extended to advance between the capsular bag and lens without the inner tube 180 without departing from the invention. FIG. 43-45 shows both the inner tube 180 and the element 116A advanced from the anterior side to the posterior side of the lens.

The element 116A may have a predetermined shape with the element 116A being in a collapsed condition in the lumen 114 and expanding toward the predetermined shape when the element 116A extends from the shaft 112. The inner tube 180 may be advanced over the element 116A to change a shape of the element 116A. For example, the inner tube 180 may have a shape that curves posteriorly as the inner tube 180 is moved out of the lumen 114. The inner tube 180 may also be advanced past the circumference of the lens and posterior to the lens.

The inner tube 180 may be advanced over the element 116A to move the element 116A to a posterior side of the lens. The inner tube 180 and the element 116A may also be advanced in multiple steps. For example, the element 116A may be advanced ahead of the tube, the tube then extended over the element 116A followed by further extension of the element 116A.

The inner tube 180 has an expanded shape that curves posteriorly as shown in FIGS. 44-47. The inner tube 180 is constrained by the shaft in a collapsed shape and expands toward the curved, expanded shape when extended from the shaft. The element 116A may be moved to dissect a posterior surface of the lens from the capsular bag as described above.

The tensioning step may be carried out with the loop 121A formed before starting the tensioning step as shown in FIG. 46. Alternatively, the loop 121A may be formed upon tensioning the element 116A if the eyelet of the element 116A is engaged before the loop 121A is completely formed. When tension is applied the loop 121A is then formed followed by the loop 121A decreasing in size to cut the lens. The loop 121A may be primarily formed by the element (to enhance cutting) by retracting the inner tube 180 prior to tensioning the element 116A. The loop 121A may also be formed by the element 116A and the shaft 112. The element 116A does, of course, extend around the loop 121A even when positioned in the shaft 112.

Figure 53:
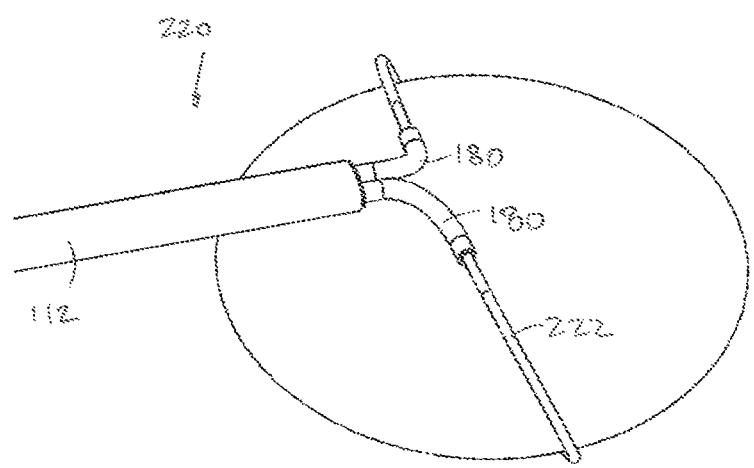
FIG. 53 shows the device of FIG. 52 with inner tubes extended from both legs.

Referring to FIGS. 48-53, another device 220 for cutting a lens within a capsular bag is shown. The device 220 has an element 116B that extends distally from the shaft 112. The element 116B has a first leg 222 and a second leg 224 which are extended simultaneously. The device 220 forms a closed loop 226 which changes orientation by at least 60 degrees, or at least 75 degrees, when the element 116B moves from the first configuration of FIG. 48 to the second configuration of FIG. 52. The orientation of the closed loop 226 changes about an axis which is transverse to the longitudinal centerline LC of the shaft when viewed along the axis 154 of the lens. The closed loop 226 may having an advancing portion 230 having a radius of curvature of at least 6 mm with the advancing portion 230 being a distalmost part of the loop 226 and extending for an angle of at least 45 degrees when the element 116B is in the second configuration. The orientation of the closed loop 226 changes without requiring a change in orientation of the shaft 112. This may be assisted through predefined shapes within the element 116B. In some embodiments, the size of the element 116B may vary along its length and for instance thicker portions may exist at the proximal root where the orientation change occurs which may provide more force to achieve the second configuration. Additionally the change may be assisted by inner tubes which may or may not extend from the lumen of the shaft 112. FIG. 53 shows the inner tubes 180 extending over the first leg 222 and the second leg 124 of the element 116B. The inner tubes 180 may be used in any manner, such as shaping the element 116B or moving the element 116 around the circumference of the lens. Furthermore, the inner tubes 180 may assist in re-orienting the closed loop 226 in the manner described herein.

The element 116B extends from the shaft 112 for a length when moving from the first configuration to the second configuration. The length may be separated into a first half and a second half extended during the first half and second half of the extension, respectively. The element 116B is shaped so that the orientation changes at least twice as much during the second half of the length as the first half of the length. Stated another way, at least 40% of the change in orientation occurs during a final 20% of the length extending from the shaft. The closed loop 226 is completely distal to the outlet 115 of the lumen 114 when the element is in the second configuration. The element 116B may be tensioned to cut the lens one the element reaches the position of FIG. 52. The element 116B may be used in combination with another device, such as the device 140, to create intersecting cuts as mentioned above Although embodiments of various methods and devices are described herein in detail with reference to certain versions, it should be appreciated that other versions, embodiments, methods of use, and combinations thereof are also possible. Therefore the spirit and scope of the invention should not be limited to the description of the embodiments contained herein. Furthermore, although the various embodiments and description may specify certain anatomical locations, species, or surgical procedures, it should be appreciated that these embodiments apply to other locations, species, and surgical procedures.

What is claimed as new and desired to be protected by Letters Patent of the United States is:

1. A method of cutting a lens within a capsular bag of an eye, comprising:
   introducing a cutting element into an anterior chamber of the eye, wherein at least a portion of said cutting element is positioned in a first, retracted configuration within a lumen, and wherein said cutting element is movable from the first configuration toward a second, expanded configuration comprising a preset, unbiased shape as the portion of the cutting element is extended from the lumen, at least part of the cutting element forming a loop with an open area as the cutting element is moved toward the second configuration;
   positioning the cutting element in the first configuration, through an opening in the capsular bag, over an anterior surface of the lens with the lens being whole and inside the capsular bag;
   extending the portion of the cutting element from the lumen to move the cutting element from the first configuration toward the second configuration, the open area increasing in size as the portion of the cutting element is extended further from the lumen, wherein the cutting element advances between the capsular bag and the anterior surface of the lens as the cutting element moves toward the second configuration;

positioning the cutting element in the second configuration around a portion of the lens between a posterior portion of the capsular bag and the lens; and tensioning the cutting element so that the lens is fully sectioned into at least two fragments.

2. The method of claim 1, wherein during said tensioning the cutting element, a posterior surface of the lens and the anterior surface of the lens are both cut with the cutting element.

3. The method of claim 1, wherein at least one of said positioning the cutting element between the capsular bag and the lens and said tensioning the cutting element comprises engaging a posterior surface of the lens and the anterior surface of the lens with the cutting element.

4. The method of claim 1, wherein said positioning the cutting element comprises rotating the cutting element to traverse a space between the capsular bag and the lens.

5. The method of claim 1, further comprising performing phacoemulsification on one or more of the lens fragments.

6. The method of claim 1, wherein the loop of said preset, unbiased shape comprises at least a first portion having a first, smaller radius of curvature and a second portion having a second, larger radius of curvature.

7. The method of claim 1, further comprising:

repositioning the cutting element around at least one of the fragments; and retensioning the cutting element to further fully section at least one of the fragments to produce smaller lens fragments.

8. The method of claim 7, further comprising performing phacoemulsification on one or more of the smaller lens fragments.

9. The method of claim 1, wherein the preset, unbiased shape is similar in shape to a cross-sectional shape of the lens.

10. The method of claim 1, further comprising removing an anterior portion of the capsular bag to form an opening in the capsular bag, wherein the cutting element is positioned over the anterior surface of the lens after the opening has been formed in the capsular bag.

11. The method of claim 10, wherein the open area of the loop of the second configuration has a dimension larger than a diameter of the opening in the capsular bag.

12. The method of claim 1, wherein the cutting element is moved between the capsular bag and the lens so that the lens is positioned in the open area of the loop.

13. The method of claim 1, wherein a shaft of a hand-held instrument comprises the lumen.

14. The method of claim 1, wherein the loop is an approximate closed loop.

15. The method of claim 14, wherein the loop is formed of the cutting element and a distal portion of the support shaft.

* * * * *